(12) United States Patent
Gaudette et al.

(10) Patent No.: US 8,691,543 B2
(45) Date of Patent: Apr. 8, 2014

(54) NANOFIBROUS SCAFFOLD COMPRISING IMMOBILIZED CELLS

(75) Inventors: Glenn Gaudette, Worcester, MA (US);
Matthew D. Phaneuf, Ashland, MA (US); Syed Ali, Westborough (MA);
Brian Almeida, Cumberland, RI (US);
Helena Alfonzo, Chestnut Hill, MA (US); Katie Flynn, Pawtucket, RI (US)

(73) Assignee: Worcester Polytechnic Institute, Worcester, MA (US)

( * ) Notice: Subject to any disclaimer, the term of this patent is extended or adjusted under 35 U.S.C. 154(b) by 534 days.

(21) Appl. No.: 12/954,829

(22) Filed: Nov. 26, 2010

(65) Prior Publication Data
US 2011/0142804 A1 Jun. 16, 2011

Related U.S. Application Data

(60) Provisional application No. 61/264,440, filed on Nov. 25, 2009.

(51) Int. Cl.
| | | |
|---|---|---|
| *C12N 11/08* | (2006.01) | |
| *A61F 2/00* | (2006.01) | |
| *C12N 11/04* | (2006.01) | |
| *C12N 5/07* | (2010.01) | |

(52) U.S. Cl.
USPC ............ 435/180; 424/423; 435/182; 435/395

(58) Field of Classification Search
None
See application file for complete search history.

(56) References Cited

U.S. PATENT DOCUMENTS

| 8,170,665 | B2 * | 5/2012 | Cohen et al. ............. 607/9 |
| 8,236,296 | B2 * | 8/2012 | Rosen et al. ............. 424/93.21 |
| 2005/0283218 | A1 * | 12/2005 | Williams ............. 607/119 |
| 2006/0200232 | A1 * | 9/2006 | Phaneuf et al. ............. 623/1.42 |

* cited by examiner

*Primary Examiner* — David M Naff
(74) *Attorney, Agent, or Firm* — Burns & Levinson, LLP; Janine M. Susan; Jacob N. Erlich

(57) ABSTRACT

The invention is directed to a device and method to prevent migration of Human Mesenchymal Stem Cells (hMSCs) from a delivery site while allowing communication between the stem cells and native cardiomyocytes. The device is characterized by scaffold pore size, fiber diameter and biomaterial selection. The invention includes a two part polyurethane scaffold that prevents migration of stem cells, allows gap junction formation through pores and is packaged for minimally invasive delivery.

15 Claims, 24 Drawing Sheets a) Side view         b) Front View

A) Schematic drawing

B) Front view

```
For L=3.0 micrometers
%E=45Pa
    E=45*(1/((1*10^6)^2));  %N/micrometer^2
    L=3;  %micrometer
    a=5;  %micrometer
    b=1;  %micrometer
    w=(266.6*(1/((1*10^6)^2))*25*pi)/3;  %N/micrometer
    I=(pi*a*(b^3))/4
        %I=3.927 micrometers^4
    d=(5/384)*((w*(L^4))/(E*I))
        %d = 41.6563 micrometers
```

A)

B)

Anti-coagulant orange)
(Scaffold(grey)
Cells (red)
Mesh (green)

C)

D)

E)

F)

ental applications. The invention is a non-degradable, cell
NANOFIBROUS SCAFFOLD COMPRISING IMMOBILIZED CELLS

RELATED APPLICATIONS

This application claims priority to and the benefit of U.S. Provisional application 61/264,440, filed Nov. 25, 2009, the contents of which are incorporated herein in their entirety.

BACKGROUND OF THE INVENTION

Heart disease is the number one cause of death in the United States accounting for one in every four deaths. Coronary heart disease is the most common type, causing the deaths of over 400,000 people in 2005. In coronary heart disease, one or more coronary arteries become occluded. The subsequent lack of oxygen and nutrients often result in permanent death of a section of heart muscle. This reduces the ability of the heart to pump blood effectively. Despite the body's compensatory measures, in many patients there is a steady decline in cardiac function until failure occurs due to a lack of native myocardial regenerative ability. Several investigators have evaluated using adult human mesenchymal stem cells (hMSCs) to repair the damaged heart muscle, via systemic infusion, direct heart infusion or by incorporation into biodegradable scaffolds. These technologies, while showing promise, are limited in their effectiveness in that: 1) systemic infusion does not target the specific damaged area of the heart, potentially leading to adverse off-target effects, 2) direct infusion does not prevent migration of the hMSCs, again potentially resulting in off-target effects and 3) use of biodegradable scaffolds for hMSC containment does not permit device removal if required.

In addition, electronic pacemakers are readily available devices that are used to solve a variety of heart problems, extending from simple heart rate and rhythm problems to complete heart failure. Even though these devices are proven to be effective, they still have a variety of limitations. Limitations include the pacemaker's battery life, sensitivity to magnetic fields, and lead failure. These drawbacks require that a patient undergo repeated operations to replace the battery; they also inhibit the patient's ability to undergo other tests such as MRIs and CT Scans. Furthermore, there are also complications related to the implantation of the pacemaker. For instance, if the pacemaker leads are improperly placed, it can cause the wrong parts of the heart to contract, resulting in inefficient pumping and in severe cases, death. Perhaps the greatest disadvantage associated with the electrical pacemaker is that it lacks the ability to provide an appropriate cardiac response when the patient is exercising or is experiencing a strong emotional reaction.

Biological pacemakers are being developed as an alternative to these electrical pacemakers with the hope of mimicking the natural pacemaker and overcoming some of the electronic pacemaker's limitations. By utilizing stem cells as a biological pacemaker, they will be capable of providing an appropriate cardiac response to exercise and emotions since the cells can react to the physiological changes in the body. Also, a biological pacemaker would not contain batteries or leads; therefore such a device is not sensitive to magnetic fields. This would provide the patient with a better alternative to cure their heart condition. Although stem cells have good qualities that allow them to be ideal for engineering biological pacemakers, there are some risks associated with them. One of the biggest risks is stem cell migration. If these undifferentiated cells were to migrate to other areas of the heart, they could cause problems like fibrillation, beating of non-cardiac muscle tissue, or cancer.

SUMMARY OF THE INVENTION

In one embodiment, the invention is a non-degradable, cell containment device that permits localized passage of secreted factors through the device wall to the surrounding tissue. The device provides a versatile and controlled method of delivering cell-based regenerative factors. Therefore, the device can be used for any cell-based protein release therapies. In one instance, insulin is produced via islet cell encapsulation within the device for treatment of diabetes.

In one embodiment, the device of these teachings includes a nanofibrous polyurethane scaffold or chamber (BioGenerator) containing stem cells, such as hMSCs. The hMSCs sustain normal function on the electrospun polyurethane surface while being contained within the device and the nanofibrous matrix is porous enough to allow for outward paracrine diffusion. Paracrines can include, but are not limited to, growth factors such as insulin-like growth factor, VEGF, or FGF. BioGenerators can be constructed to contain cell types that produce other therapeutic or regenerative factors, including but not limited to hormones, peptides, proteins, or antibodies.

In one instance, the nanofibrous polyurethane (nPU) delivery device is a non-degradable delivery platform allowing greater control of treatment location and time since the device can be placed at the exact site of damage and is easily removable. In one instance, the nanofibrous scaffold is made by electrospinning technology which creates structures similar to natural extracellular matrix in size and scale, thereby providing hMSCs with a familiar environment.

In one embodiment, the device of these teachings includes a scaffold or chamber that will hold stem cells which are to be used as a biological pacemaker for implantation into the heart. The scaffold, which will be implanted within the ventricular septum via a minimally invasive approach, will immobilize the cells and prevent them from spreading to other areas of the heart or body. The scaffold will contain pores large enough to allow the stem cells to form gap junctions with neighboring myocytes, but small enough that they keep the stem cells within the container. This invention will not impede the formation of these gap junctions, which are necessary to propagate an electrical current through the heart. The scaffold will be durable enough to withstand the normal contractile forces that are associated with heart function. The scaffold will be placed adjacent to living cardiomyocytes, and therefore, should not impede the normal physiological functions of these cells.

DETAILED DESCRIPTION

The device of the teachings herein, referred to as the "Bio-Generator", is a device to encapsulate hMSCs while allowing factors they secrete to diffuse through the capsule. There are several distinct advantages for utilizing this device over previous delivery methods in that this system: provides targeted delivery of hMSCs eliminating any need for cell homing; delivers factors directly to the infarct site eliminating any need for large numbers of human MSCs due to potential off-target delivery; localizes human MSCs directly to one area eliminating or minimizing off-target effects; is minimally invasive; deliverable by catheter; and is removable.

Figure 1:
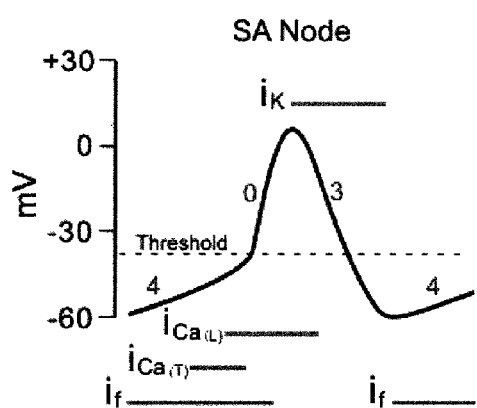
FIG. 1 is a graph of the electric potential of a pacemaker.
Figure 2:
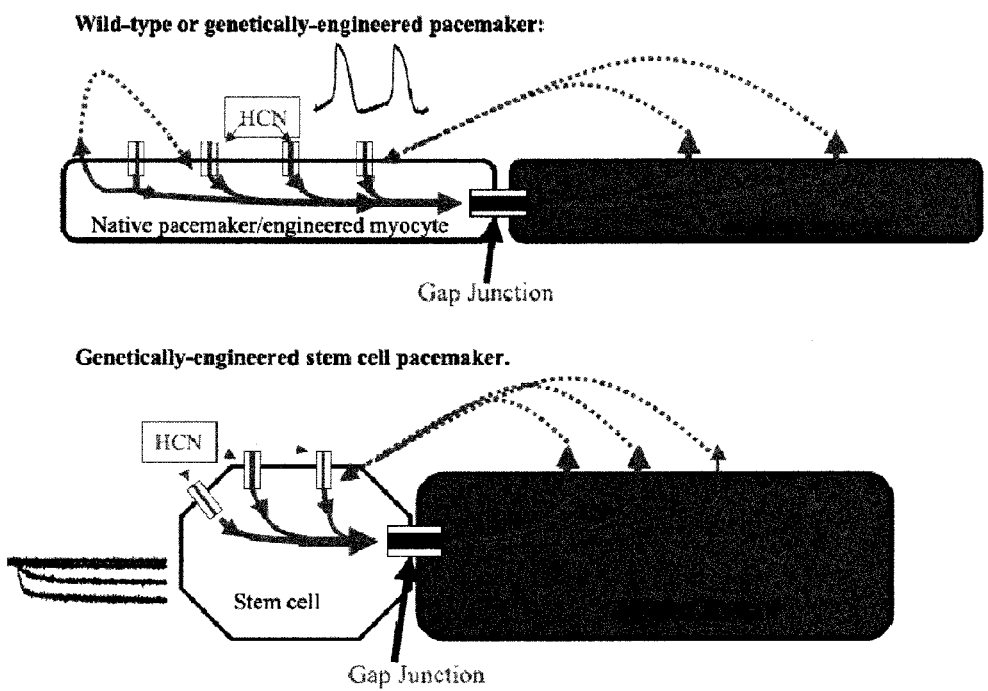
FIG. 2 is a diagrammatic representation of a wild-type or genetically-engineered pacemaker (myocyte-myocyte gap junctions, top panel) and a genetically-engineered stem cell pacemaker (stem cell-myocyte gap junctions, bottom panel)

One embodiment of the invention is a Human Mesenchymal Stem Cell (hMSC) driven Biological Pacemaker. In a normal pacemaker cell, the cell's own depolarization initiates an action potential in the cell. This action potential is then transmitted to other cells via gap junctions, passing down the current. For adult mesenchymal stem cells to mimic this natural depolarization, the cells would have to be modified in order to express an HCN isoform. The HCN (Hyperpolarization-activated cyclic nucleotide gated) channels open in response to depolarization after an action potential. The opening of these channels allows an influx of sodium ions which is the cause of the spontaneous repolarization seen in FIG. 1. The sodium ions then flow to the adjacent myocytes through gap junctions as seen in FIG. 2. In the top panel of FIG. 2, the action potential current is initiated purely by adjacent myocytes, whereas in the bottom panel, adjacent myocytes initiate the stem cell's action potential. This occurs until threshold for the myocyte action potential is reached. The action potential is propagated to other myocytes through the gap junction chain. This mechanism allows for the synchronization of the depolarization current to the diastolic current, creating an on/off switch for the current to fire. In this case, both the stem cell and the adjacent cardiomyocyte would work as a pacemaker. The advantage of this method is that this approach does not need the stem cell to differentiate into a pacemaker cell in order to perform its function.

Figure 3:
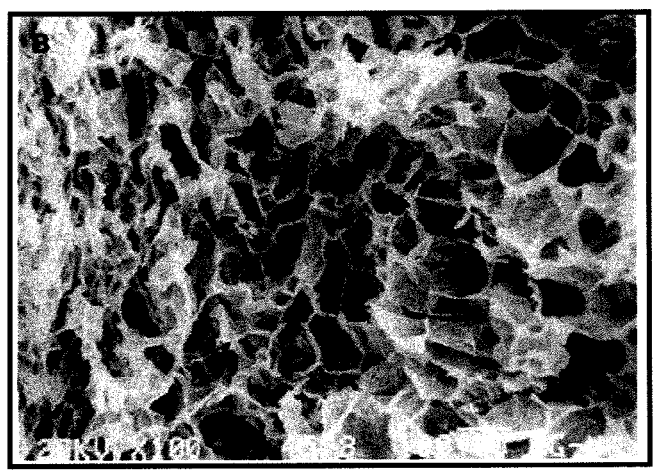
FIG. 3 is a scanning electron micrograph of a scaffold.

If dissociated cells are injected into the body it can be nearly impossible to control the shape, size, and location of the implanted cells. In order to help control these factors, different types of scaffolds are employed. These scaffolds work as a support frame for cells to attach to and grow (see FIG. 3). In order to keep the cells alive, the scaffold must permit the diffusion of cell nutrients and other molecules important for proper cell function. In the case of an implant, the scaffolds can be used to not only deliver cells, but biochemical factors as well. Another advantage of scaffolds is their ability to manipulate cell behavior by applying a series of mechanical and biological stresses. The biggest challenge posed by the use of scaffolds is the lack of cell migration into the 3-D structure. This is a problem because in healthy myocardial tissue, cells are considerably dense when compared to other tissue including cartilage and vascular tissue.

Different materials can be used to create these scaffolds depending on the mechanical conditions having to be withstood. The main materials used for scaffolds containing cardiac cells can be synthetic or biological. The synthetics include woven nylon (PET—also known as Dacron), polytetrafluoroethyline (ePTFE), poly(glycolic acid) (PGA), gelatin and alginate). Biological materials like gluteraldehyde-cross-linked biological membranes, bovine tissue, and collagen scaffolds are also used.

There are several different ways of synthesizing tissue engineering scaffolds. One process is nanofiber self-assembly. The main advantage of this method is that the biomaterials created with this method develop properties similar to those of natural extracellular matrix (ECM). This similarity allows the scaffold to be more biocompatible than other scaffolds, including those derived from animal tissue.

Figure 4:
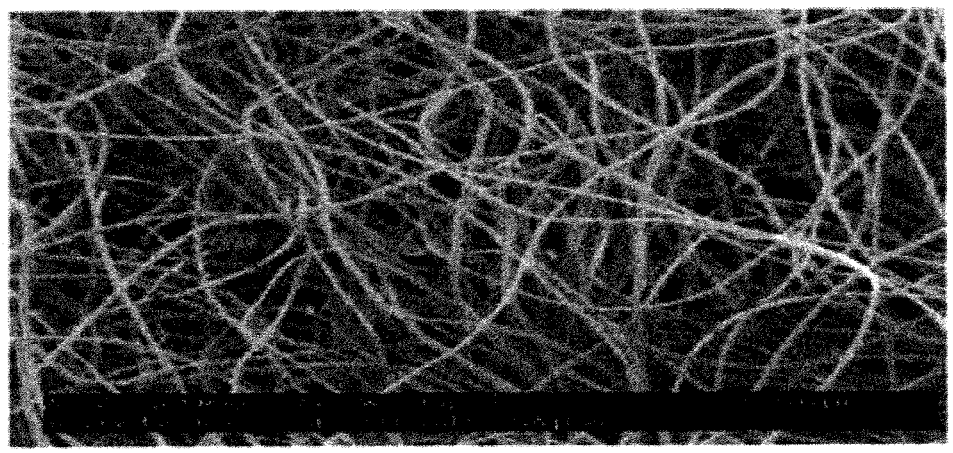
FIG. 4 is a high magnification photograph of a non-woven mesh of PGA fibers.

Another way that these scaffolds can be synthesized is by using textile technologies. This process is used when nonwoven meshes of different polymers are desired (see FIG. 4). These have been used successfully in growing different types of cells. The drawback of this method is that it is hard to control pore size and level of porosity.

Solvent casting and particulate leaching is an additional way of synthesizing scaffolds. This method allows tissue engineers to control the porosity of the scaffold providing a material with a regular pore pattern. The drawback is that there is a limit on how thick the scaffold can be. Solvent casting starts by mixing the desired polymer into an appropriate organic solution. The solution is then poured into a mold and some porogens are added to the mix. Porogens are particles like sodium chloride, saccharose, or gelatin that are added to the solution before it sets. When these particles are removed they will give the scaffold its desired porous properties, including the size and amount of pores found in the scaffold. Once the polymer has been casted, the solution is allowed to evaporate leaving the polymer scaffold with the porogens still embedded in it. In order to remove the porogens, the scaffold is submerged in a liquid that dissolves the particles. Another drawback of this process is if all the porogens are not completely removed from the material, then these particles can damage the cells that are implanted onto the scaffold.

Scientists have tried to overcome the drawbacks of the solvent casting and particulate leaching process by creating new means of making these 3-D structures. To avoid the damage caused by the porogens that were not properly dissolved, they have moved from solid porogens to gas porogens. This process called gas foaming starts by creating a disc shaped mold out of the preferred polymer by means of compression molding with heat. In order to make the material porous, the disc is placed into a chamber where $CO_2$ at high pressures is pumped in. The discs remain inside for a couple of days and then the chamber is slowly decompressed back to atmospheric pressure. During their time in the chamber, the discs are allowed to absorb the $CO_2$ which create the desired porous 3-D matrix. Once all the $CO_2$ is removed, the structure maintains its shape. Although this process solves the problem caused by not fully dissolved porogens, it still has some disadvantages. The main drawback of this process is that the heat used during the compression molding part of the scaffold formation limits the materials that can be utilized (Ma, 2005).

Figure 5:
FIG. 5 is a high magnification photograph of polyurethane fibers produced by electrospinning.

Another method of creating scaffolds is electrospinning, which uses high voltages in combination with distance from the material source to the base in order to produce a cross-linked mesh. It can produce polymer fibers of nanometer to micrometer size in diameter; FIG. 5 shows 1.0 μm polyurethane fibers that were produced via electrospinning. In a study performed by Angelo Pedicini et al., the authors electrospun the polyurethane solution from a 1 mL glass pipette with a capillary tip of approximately 1 mm inner diameter. A stainless steel electrode was placed in the polymer solution. These were spun onto a grounded aluminum foil sheet (Angelo Pedicini et al., 2003).

Figure 6:
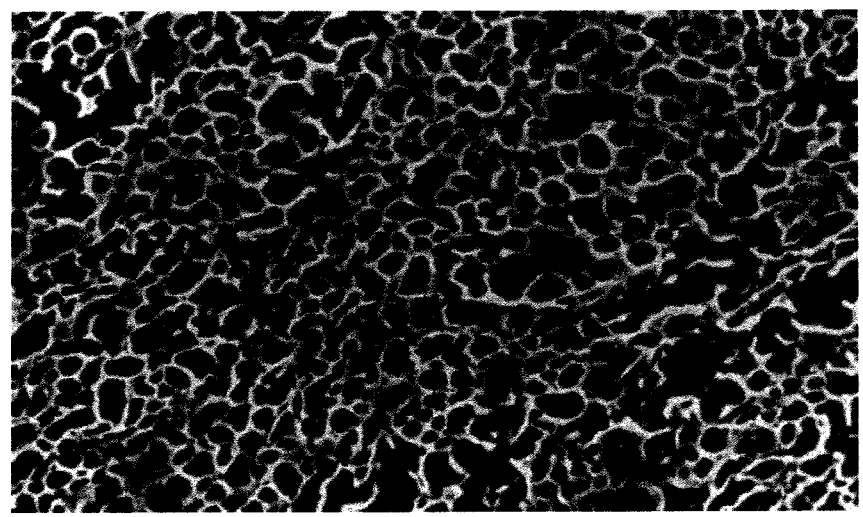
FIG. 6 is a scanning electron micrograph showing the microporous structure of polyurethane.

A possible method for producing a biomaterial with pores was done by Ze Zhang et al. The authors prepared a 7% (w/v) polyurethane solution by dissolving polyurethane pellets in 1,4-dioxane. They used phase inversion and freeze-drying to prepare the polyurethane tubes in an external cooling fashion. A glass capillary was inserted into a glass tube to form a casting mold, and then the polyurethane solution was poured into the space between the two glass tubes. Various cooling treatments were used for the polyurethane solution to become a solid; pore size is dependent upon the cooling rate. To remove the solvent, the mold was freeze-dried. Once the polyurethane was removed, it was sterilized in 70% alcohol (Zhang et. al., 2003). FIG. 6 shows the microporous structure of polyurethane by using this methodology.

One embodiment of the invention is directed to a scaffold that will hold stem cells which are to be used as a biological pacemaker for implantation into the heart. The scaffold, which will be implanted within the ventricular septum via a minimally invasive approach, will immobilize the cells and prevent them from spreading to other areas of the heart or body. The scaffold will contain pores large enough to allow the stem cells to form gap junctions with neighboring myocytes, but small enough that they keep the stem cells within the container. This invention will not impede the formation of these gap junctions, which are necessary to propagate an electrical current through the heart. The scaffold will be non-degradable and durable enough to withstand the normal contractile forces that are associated with heart function. The scaffold will be placed adjacent to living cardiomyocytes, and therefore, should not impede the normal physiological functions of these cells.

In one instance, the scaffold inhibits cells from migrating away from designated target location. The scaffold functions as a physical barrier to migration. Inhibition of migration can also be enhanced by chemical treatment of the scaffold. Inhibition of migration can be enhanced by incorporating extra-cellular matrix proteins and peptides into the scaffold, including, but not limited to, RGD peptides, collagen, fibrinogen, fibrin, laminin and combinations thereof.

The scaffold allows or facilitates formation of gap junctions, which are essential for the propagation of an electrical signal. The scaffold can be implanted into the ventricular septum, and is strong enough to withstand contractile forces of the heart. The device of the invention supports malfunctioning or damaged areas of the heart by allowing cells encapsulated within the scaffold chamber to pace the heart. The scaffold does not interfere with normal physiological functions will be placed within close proximity of living myocytes in the patient and does not impede electrical activity of the myocytes.

Cells cannot pass through the mesh; pore size will be 0.5-10 micrometers depending on the size of the cell to be contained within the scaffold. For hMSC's the pore size is preferably less than 3 micrometers. Pore size can be about 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 μm in diameter. The pore size can be a range of these diameters. The thickness of the nanofibrous scaffold can also be adjusted as needed. The thickness can be 10-150 μm. Thickness can be about 10, 20, 30, 40, 50, 60, 70, 80, 90, 100, 110, 120, 130, 140, 150 μm. Preferred thickness to promote gap junction formation is 10-20 μm. Thickness can be a range of these parameters.

Stem cells contained within the device must contact myocytes to allow gap junction formation. Preferably, gap junctions should be able to form within 48 hours of implantation.

The scaffold does not degrade or break free and is biologically inert and biocompatible. The size of the device is large enough to seed the needed amount of cells for the desired treatment or use within a patient's body. A range of about 100,000 to 1,000,000 stem cells is used for electrical repair of the heart. For paracrine related repair or treatment, of the heart or other organs or tissues a range of about 100,000 to 3,000,000 cells will be contained within the scaffold.

The device will be implanted by means of minimally invasive surgery, for example via a catheter.

"Degradability" is the ability of the material to breakdown in a controlled manner and be absorbed by the body.

"Biocompatibility" means the material causes little to no immune response (this includes minimizing the formation of scar tissue around the scaffold).

"Immobilization" means keeping the cells inside the scaffold rather than allowing them to migrate around the heart or other areas of the body.

"Allowing gap function formation" means gap junctions form between genetically engineered stem cells and the patient's native cardiomyocytes in order to communicate with cardiomyocytes allowing the genetically engineered stem cells to pace the heart.

"Myocardium attachment" means the device scaffold will attach to the heart (either inside of the heart wall or just placed on the wall surface).

"Mechanically stable" means the material will not break down or deform due to the mechanical forces experienced when implanted in the heart.

"Removability" means the scaffold's ability to be removed after implantation in the event of any complication or cessation of any treatment.

In order to contain MSCs and allow the formation of gap junctions, the scaffold material must be porous. Pore size is critical; it must be large enough to allow for the passage of electrical signals yet not too large to permit leakage of stem cells (Rosen et ad, 2004). Other factors beyond the diameter of the pore must be considered as well. When a biomaterial is subjected to compressive stress, the average size of the pores will decrease and thus the permeability of the material will lessen (O'Brien et al 2007). A study by O'Brien et al. concerning the porosity of a scaffold and its effects on stem cells showed that with increased pore size and permeability, greater levels of metabolic diffusion occur and consequently induce stem cell proliferation (O'Brien et al 2007).

The scaffold must be strong enough to withstand the contractile/relaxation motion of the heart, yet flexible and adaptable to allow mesenchymal stem cells to proliferate. A scaffold material subjected to the systolic and diastolic pressure must withstand forces higher than 120/80 mmHg respectively, to ensure that it will not break under repeated contractile and relaxation forces.

The scaffold material must also be flexible to allow mesenchymal stem cell proliferation and ease implantation. The stem cells must be able to proliferate within the scaffold to ensure that as old cells die, new ones are generated to facilitate the communication with cardiac myocytes. Over-proliferation is not a concern in the design of the scaffold as MSCs are attachment dependent: they will adhere to the inner wall of the scaffold and will not be concentrated in the center. As a result, this cell distribution will not impose any mechanical stress on the scaffold that could potentially cause it to burst.

Lastly, the material must be simple to implant into the ventricular septum through the use of a catheter. This minimally invasive approach will require a flexible and injectable material to effectively be inserted.

One embodiment of the device is a fibrous crosslinked scaffold. Another embodiment is a hollow scaffold with pores. Both can be in the shape of a football, with the inside being hollow to allow cells to be held inside. Both designs maximize the surface area with which the modified hMSCs could form gap junctions with cardiac myocytes. The main difference between the designs depends on the manufacturing technique: the cross-linked scaffold is electrospun while the alternative design utilizes solvent casting or particulate leaching.

Figure 7:
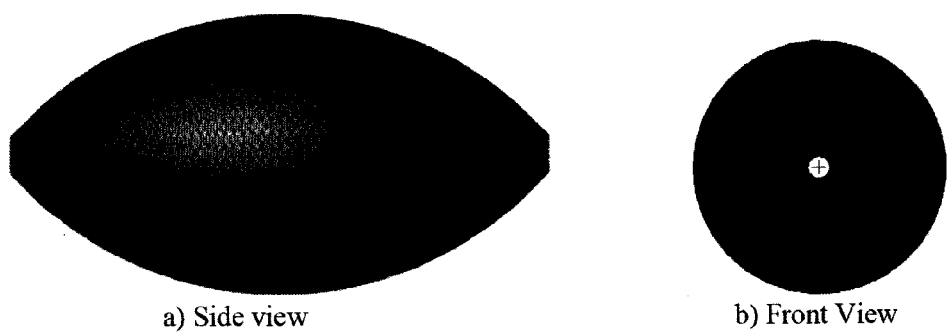
FIG. 7 is a diagram of a cross-linked scaffold of the invention, A) shows a side view and B) shows a front view.

One conceptual design is a cross-linked scaffold. For this design, the fibers of the biomaterial will be interwoven via electrospinning (see FIG. 7; note: the diagram is not scaled to size). For this design the material will first be electrospun into the football shape; this shape allows for a maximized surface area for the cells to attach to in order to form gap junctions. The cells are then injected through the ends of the scaffold.

Figure 8:
FIG. 8 is a diagram of a scaffold with pores, A) is a schematic drawing and B) shows a front view.
Figure 8:
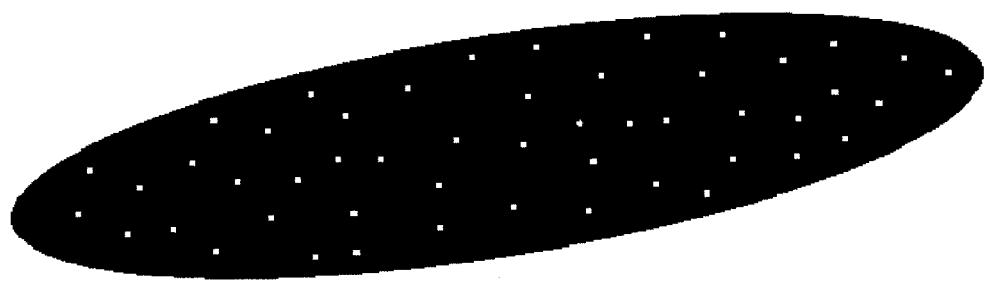

The second conceptual design is a scaffold that contains a hollow interior with scattered pores located on all sides of the exterior (see FIG. 8; note: the diagram is not scaled to size). The hMSCs will be placed on the inside of this scaffold, allowing for gap junction formation through the pores. One advantage this design has over the electrospun design is that the pore size can be more controlled and concise since it will be produced using solvent casting or particulate leaching.

In order to appropriately choose a material capable of withstanding the mechanical stresses of the heart, preventing human mesenchymal stem cell migration and other complications, common materials being employed in cardiovascular applications were evaluated. The three most common materials utilized for the production of synthetic vascular grafts are Polyethylene Terephthalate (PET) also known in the medical industry as Dacron, Polytetrafluoroethylene (PTFE), and Polyurethane (InspiredMD Corporation, 2005). In addition, Nitinol is a main component of various vascular stents. Table 1 summarizes the material properties. A summary of the materials' characteristics under each condition evaluated can be found in Table 2.

TABLE 1

Summary of Candidate Material Properties

|  | Nitinol | Dacron (PET) | ePTFE | Polyurethane (ChronoFlex ® C) |
|---|---|---|---|---|
| Biocompatible | Yes | Yes | Yes | Yes |
| Cytotoxic | No | No | No | No |
| Elastic Modulus | 1160-1200 × 10$^4$ psi | 40-60 × 10$^4$ psi | 5.8-8.01 × 10$^4$ psi | 0.775-1.9 × 10$^4$ psi |
| UTS | 28.3-100 ksi | 7.01-10.5 ksi | 2.9-4.35 ksi | 5.5-7.5 ksi |
| Yield Strength (Elastic limit) | 179-276 ksi | 8.19-9.04 ksi | 2.18-3.63 ksi | — |
| Multiaxial fatigue | — | 2.8-4.2 ksi (at 10$^7$ cycles) | 0.834-1.02 ksi (at 10$^7$ cycles) | — |
| Shear Modulus | 4.35-4.69 × 10$^6$ psi | 0.144-0.216 × 10$^6$ psi | 0.02-.0276 × 10$^6$ psi | — |

TABLE 2

Qualitative Material Description

| Material | Mechanical Properties | Bio/Hemo-compatibility | Corrosion & wear resistance | Availability | Ease of manufacturing |
|---|---|---|---|---|---|
| Dacron | May kink | Susceptible to fibrotic encapsulation and infection | Can degrade | X | Easy |
| Nitinol | Shape memory, strong | Excellent | Oxide layer protects surface from corrosion and degradation | + | Fair |
| ePTFE | Change drastically over time | Can ward off infections | Can degrade | + | Fair |
| Polyurethane | Durable, resistant to fatigue, elastic and compliant to surrounding cardiac tissue | Not cytotoxic to cells, no thrombus formation observed, resistant to bacteria | Does not degrade over time (durable) | + | Easy |

Table 3 shows the results stated above just as positive (+) and negative (−) signs to represent the material's performance under each category.

TABLE 3

Material Summary

| Material | Mechanical Properties | Bio/Hemo-compatibility | Corrosion & wear resistance | Availability | Ease of manufacturing | Total |
|---|---|---|---|---|---|---|
| Dacron | − | − | − | − | + | 1 |
| Nitinol | + | + | + | + | − | 4 |
| ePTFE | − | + | − | + | − | 2 |
| Polyurethane | + | + | + | + | + | 5 |

The preferred material is polyurethane as the material for the cardiac scaffold based on the material's mechanical properties, biocompatibility, corrosion and wear resistance, cost, availability, and manufacturability to the desired specifications.

Polyurethane is available commercially as Chronoflex® C developed by AdvanSource Biomaterials. Chronoflex® C is an aromatic thermoplastic polyurethane especially designed for biodurability by preventing surface degradation caused by stresses from the surrounding environment (ChronoFlex, 2008). If needed, this material could be compounded for radiopacity (ChronoFlex, 2008), allowing for tracking of the scaffold after implantation through imaging technologies.

Mechanical Calculations Deflection of a hMSC

Based on the pore-size testing results, the pore size of the electrospun polyurethane should be between 0.4-3.0 μm. To obtain an optimum pore-size approximation, the deflection of an hMSC was calculated mathematically at different pore-sizes.

In order for gap junctions to occur, both the pore size and fiber diameter need to be balanced so that cells on opposite ends of the fiber deflect and touch each other. If these two parameters are not appropriately balanced, either the cells will not come into contact with each other or the cells will migrate through to the opposing end of the fiber.

Figure 9:
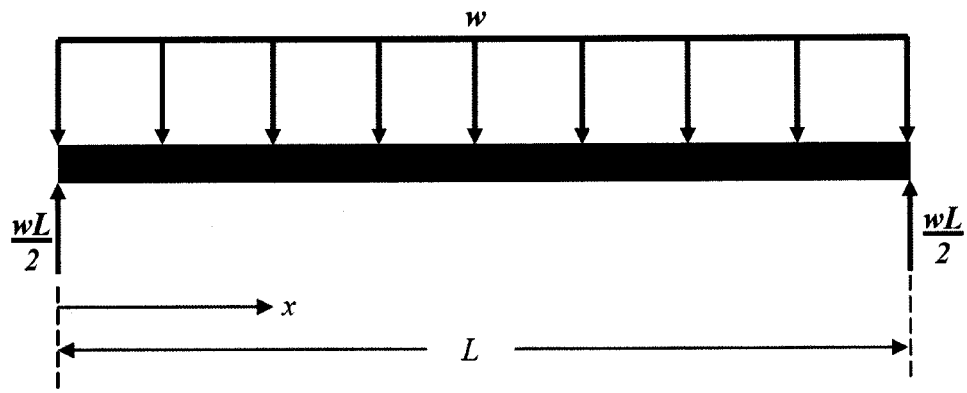
FIG. 9 is a free body diagram of a hMSC.

From literature, it was determined that a cell has a length of 10.0 μm and a thickness of 2.0 μm (Tastan, et. al., 2009). It was also assumed that there was a uniform load distribution on the cell caused by the beating heart (see FIG. 9).

Maximum deflection occurs at x=L/2; therefore the maximum deflection equation is:

$$\Delta_{max} = 5wL^4/384EI \qquad \text{Eq. 1}$$

where E is the Young's Modulus of a hMSC, I is the moment of inertia of the hMSC, L is the length between fibers (the pore-size), and w is the force per unit length. The constants obtained from literature were Young's Modulus and the pressure exerted by the intramyocardial wall. In a study conducted by Tan, et. al. (2008), it was determined that at human body temperature (37° C.), the Young's Modulus of an hMSC is 126±81 Pa. For the intramyocardial pressure constant, Heineman et. al. (1985) determined that there was a range of 5±2 mmHg. The mean value (5 mmHg) was then used to determine the force per unit length exerted onto the cell at various pore sizes.

Figure 10:
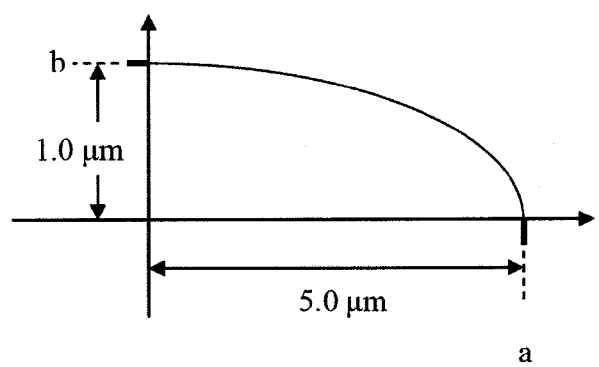
FIG. 10 is a graph of the moment of inertia of a hMSC.

To calculate the moment of inertia, it was assumed that the shape of the cell is elliptical. For a quarter of an ellipse, the moment of inertia equation is:

$$I = \pi a b^3 / 16, \qquad \text{Eq. 2}$$

where a and b are defined in FIG. 10.
Therefore, the moment of inertia equation for a full ellipse is:

$$I = \pi a b^3 / 4. \qquad \text{Eq. 3}$$

The resulting moment of inertia of a hMSC is 3.93 μm$^4$.

Figures 11, 12:
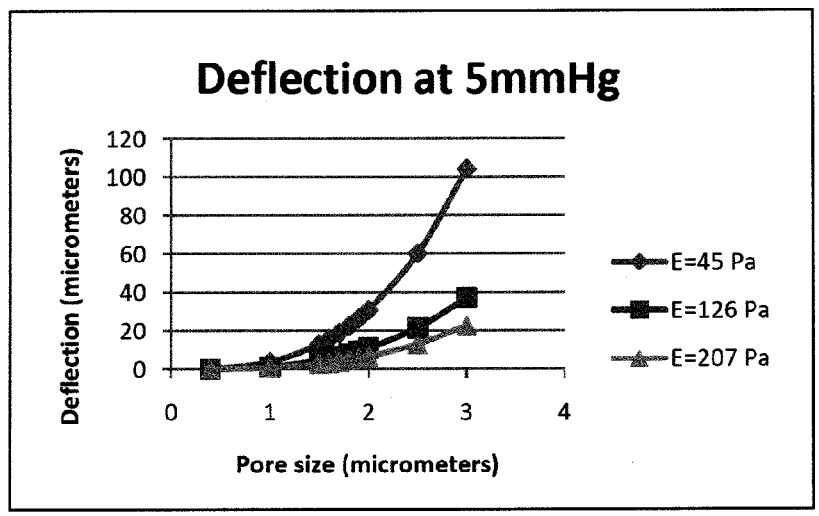
FIG. 11 is a snapshot of the syntax used in Mat Lab.
FIG. 12 is a graph of deflection of a hMSC versus pore size and Young's Modulus.

The last variable included in the maximum deflection equation, L, varied from 0.4 to 3.0 μm. For the calculation, increments of 0.5 were used from 1.0 to 3.0 μm; no increments were used between 0.4 and 1.0 μm. The calculations for the maximum deflection were completed using MatLab. An example of the syntax used in MatLab is shown in FIG. 11.

Based on these calculations, the most desirable pore-size for hMSC's is between 2.0 and 2.5 μm (see Tables 4A and 4B) because it would result in a more manageable fiber thickness. The average deflection length between 2M and 2.5 μm is 15-30 μm. Therefore, the fiber diameter would need to be double the deflection length in order to account for cells deflecting on opposite sides of the fiber and forming gap junctions. As a result, the fiber thickness should be approximately 30-60 μm.

Tables 4A & 4B: Calculation Results

TABLE 4A

Length between Fibers = 2.0 μm

| Pressure (PA) | E(Pa) | d (μm) |
|---|---|---|
| 133.3 | 45 | 6.16 |
| 133.3 | 126 | 2.2 |
| 133.3 | 207 | 1.34 |
| 266.6 | 45 | 12.34 |
| 266.6 | 126 | 4.41 |
| 266.6 | 207 | 2.68 |
| 666.6 | 45 | 30.86 |
| 666.6 | 126 | 11.02 |
| 666.6 | 207 | 6.71 |
| 799.9 | 45 | 37.03 |
| 799.9 | 126 | 13.23 |
| 799.9 | 207 | 8.05 |

TABLE 4B

Length between Fibers = 2.5 μm

| Pressure (PA) | E(Pa) | d (μm) |
|---|---|---|
| 133.3 | 45 | 12.03 |
| 133.3 | 126 | 4.3 |
| 133.3 | 207 | 2.61 |
| 266.6 | 45 | 24.11 |
| 266.6 | 126 | 8.61 |
| 266.6 | 207 | 5.24 |
| 666.6 | 45 | 60.28 |
| 666.6 | 126 | 21.53 |
| 666.6 | 207 | 13.1 |
| 799.9 | 45 | 72.33 |
| 799.9 | 126 | 25.83 |
| 799.9 | 207 | 15.72 |

FIG. 12 represents the correlation between the length between fibers and the Young's Modulus. As the pore size increases, the deflection also increases; as Young's Modulus increases, the deflection decreases.

To create a biological pacemaker, Brink, Cohen, Rosen and Robinson have transfected mesenchymal stem cells (MSCs) with pacemaker genes. These genes encode for the incorporation of ion channels in the MSC membrane. When these cells are delivered to the heart, they form gap junctions with the native cardiac myocytes. Ions can then flow into the genetically altered MSCs and through the gap junctions into the myocytes. This ion flow into the myocytes can cause the myocyte to depolarize, thereby initiation a heartbeat. The two cell unit effectively forms a pacemaker. It is important to contain the transfected MSCs to the delivered region, while allowing them to form gap junctions.

The number of modified hMSCs required to replace the function of the sinoatrial node is estimated to be 350,000 cells to fully restore function, but with only 50% transfection efficiency 700,000 are injected. Therefore, in order to seed 700,000 hMSCs onto the scaffold the area of the cell mass and the surface area of the scaffold were calculated to determine appropriate dimensions for the scaffold.

The following formula was used to determine the surface area needed for 700,000 cells:

$$A_{cell} = 7\pi r^2 * 700,000. \qquad \text{Eq. 4}$$

The calculated surface area is 55.0 mm$^2$ for 700,000 cells.

Figure 13:
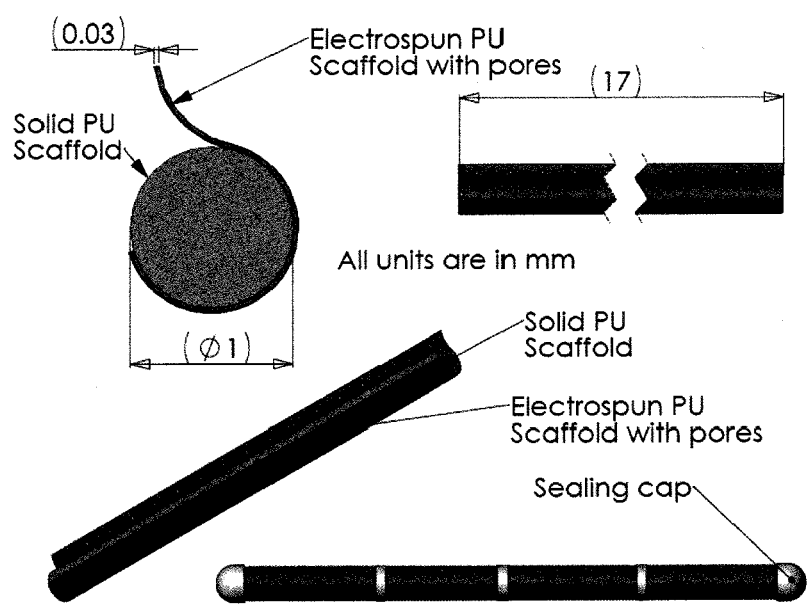
FIG. 13 is a diagrammatic representation of a two-part cylindrical scaffold.

Based on the migration assays, the mechanical calculations, considerations for minimally invasive delivery through a catheter, and development of the nPU sheets described herein, one example of a design for the device is depicted in FIG. 13. The design consists of a two part cylindrical scaffold. The cylindrical shape was chosen because it resembled the shape of scents, which are widely used in the cardiac industry. The blue section is a solid cylinder composed of ChronoFlex® C. The purpose of this solid cylinder is to provide mechanical support to the scaffold. The red section represents a porous electrospun ChronoFlex® C film on which the modified hMSCs are seeded. This membrane is thin enough to allow for cellular communication across the scaffold and the pores are sized to prevent cells from migrating through to the other side. After cellular adhesion, the porous film is wrapped around the solid polyurethane cylinder. To finalize the scaffold, sealing bands and caps in conjunction with BioGlue® are added to prevent hMSC migration out of the scaffold from the sides of the cylinder. Another function of the sealing bands and caps is to protect the porous membrane from any shear stresses to the scaffold during delivery.

Using current cardiac catheter sizes as a guide to develop the scaffold, the solid polyurethane component of the design should have an outer diameter of about 1.0 mm. The minimum length of the scaffold was then calculated taking into consideration the amount of surface area needed to seed 700,000 cells (amount of cells seeded to induce pacemaker function in the heart) onto the surface of the porous membrane. Because the electrospun polyurethane is in the shape of a cylinder; the following surface area equation was used:

$$SA_{cylinder} = 2\pi r^2 + 2\pi r l,$$ Eq. 5 where r is the radius of the solid polyurethane scaffold, SA is the surface area of the 700,000 cells and l is the minimum length of polyurethane needed. It was determined that the length needed was 17.0 mm.

The deflection calculations determined that the desired electrospun membrane thickness was between 30 and 60 μm, and from both the deflection calculations and the pore size migration assay it was determined that the optimal pore size is between 2.0 and 2.5 μm.

In order to seal the scaffold sealing bands and caps in conjunction with BioGlue® can be used. BioGlue is a surgical adhesive developed by CryoLife that has been specially designed for use in cardiovascular surgery. It is composed of purified bovine serum albumin (BSA) and gluteraldehyde that are packaged in two separate chambers of a syringe.

When the BioGlue is delivered, the two components mix and the materials are cross-linked creating a flexible mechanical seal that does not depend on the body's clotting mechanism. Polymerization begins within 20 to 30 seconds after mixing, and at two minutes, it is strong enough to bond things together. This adhesive is useful for bonding biological tissue as well as synthetic grafts because it bonds within the interstices of the graft matrix.

Pore Size Migration Assay

Migration of non-terminally differentiated stem cells from target sites is a current concern with stem cell based therapies. The migration of modified hMSCs migrating away from the heart and differentiating could cause unpredictable effects on the body. A direct effect could be multiple concentrations of modified hMSCs settling at different sections of the heart. This could mean multiple action potentials initiating simultaneously at different locations of the heart resulting in fibrillation. For these reasons limiting and ideally preventing migration all together is a key function of the design.

Figure 14:
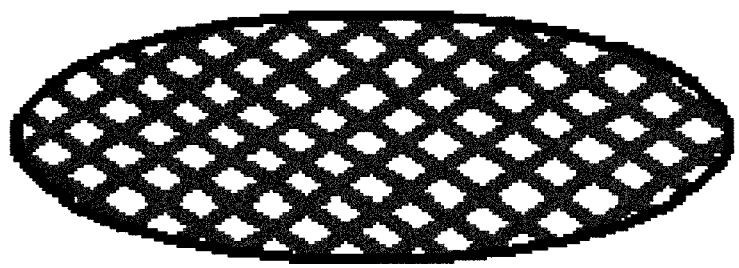
FIG. 14 is a diagrammatic representation of a stem cell scaffold.
Figure 15:
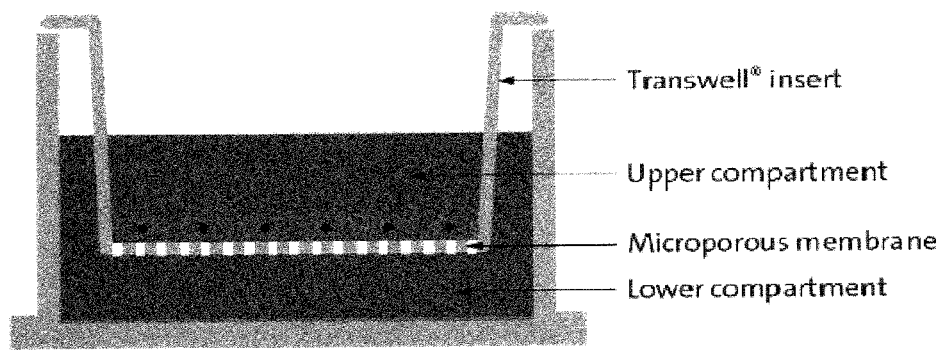
FIG. 15 is a diagrammatic representation of the pore size test wells.

To limit migration, a porous mesh was created (See FIG. 14). An integral aspect of this design is the pore size of the mesh. Ritter et. al, investigated the migratory effects of Basic Fibroblast Growth Factor (FGF-2) on human mesenchymal stem cells (2008). In a Transwell migration assay (Boyden assay), they found hMSCs migrated through 8 μm pores when FGF was used as a chemoattractant in excess of 20 ng/mL. Although Ritter et. ad, found that breast cancer derived FGF-2 and Vascular Endothelial Growth Factor (VEGF) both induced attractive migration of human mesenchymal stem cells, in vitro concentrations were similar and FGF-2 costs less to obtain (Invitrogen, Carlsbad, Calif.). In addition to 8 μm pores, 3 μm and 0.4 μm pore Transwells (NUNC, Rochester, N.Y.) were tested to determine the pore size at which hMSCs cannot migrate. See FIG. 15 for test representation. A concentration of 30 ng/mL placed in the lower compartment with 400 μL of DMEM media simulated double the physiological concentration of FGF-2. 100,000 hMSCs were seeded on the upper part of the microporous membrane and incubated for 3 days at 37° C. and 5% CO2. Migration of cells was quantified using Hoechst and Phalloidin staining for cell nuclei and cytoplasm, respectively.

Results: Trial 1

Figure 16:
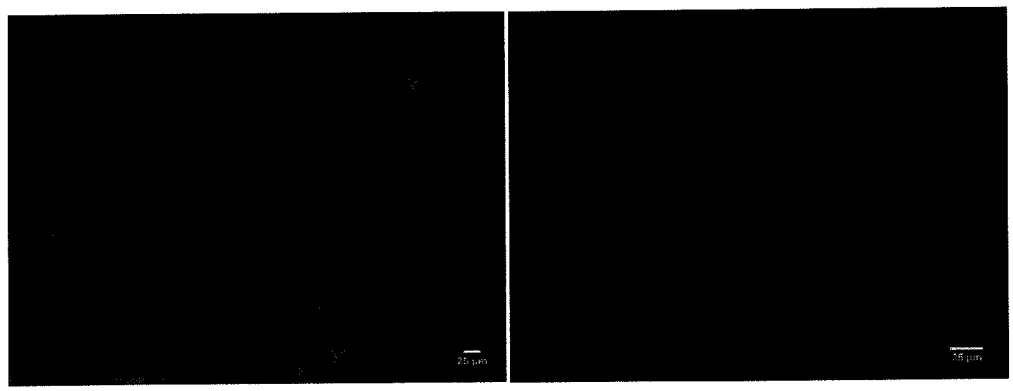
FIG. 16 is photographs of stained cells using the 8 μm insert of the bottom of the insert (left) and bottom of the well (right)

For the first trial of the pore size migration assay, three separate items were stained: the bottom of the wells after 3 days of incubation, the bottom of the wells after 11 days of incubation, and the well inserts themselves after 11 days of incubation. Staining of the wells used for the 8 μm pore inserts showed that only 3-4 hMSCs passed through after 3 days of incubation; however, after 11 days, a significantly larger amount of cells had passed through. In some of the wells, over 20 hMSCs had migrated through. With the 3 μm inserts, only 1-2 cells were seen in the wells for both 3 and 11 days worth of incubation. Staining of the wells used in conjunction with the 0.4 μm inserts showed no signs of cell migration. FIG. 16 shows images that were obtained from the first trial.

Based on the results, the proper pore size for hMSC's is between 0.4 μm and 3 μm. While a minimal amount of cells passed through the 3 μm pores, no cells passed through the 0.4 μm pores. Therefore, the preferred pore size for hMSC's is around 1 μm to 2 μm.

Results: Trial 2

The second trial of this assay had a similar setup to the previous run, but with only 0.4 micron and 3 micron porous wells. Again, a FGF based chemoattractant was used to help induce migration of the hMSCs (approximately 55 ng/mL) and roughly 50,000 cells were allowed to incubate within the wells for 3 days before the staining procedures were carried out. The limitations associated with the initial trial of the Migration Assay were also addressed in this run. In order to have some experimental control, both a positive and negative control were used in order to more accurately identify the migration of a stem cell through a pore. For the positive control, hMSCs were seeded on the reverse side of the well; for the negative control, only media was put into the well.

The other major drawback with the initial trial was addressed in how the wells were analyzed. The initial run looked at cells which had completely passed through the well and seeded to the bottom of the plate. However, it is more likely for the stem cells to migrate from the upper side of the well to the lower portion through the porous membrane. In order to identify this style of migration, the wells were examined prior to and after scraping the upper portion of well membrane.

Figure 17:
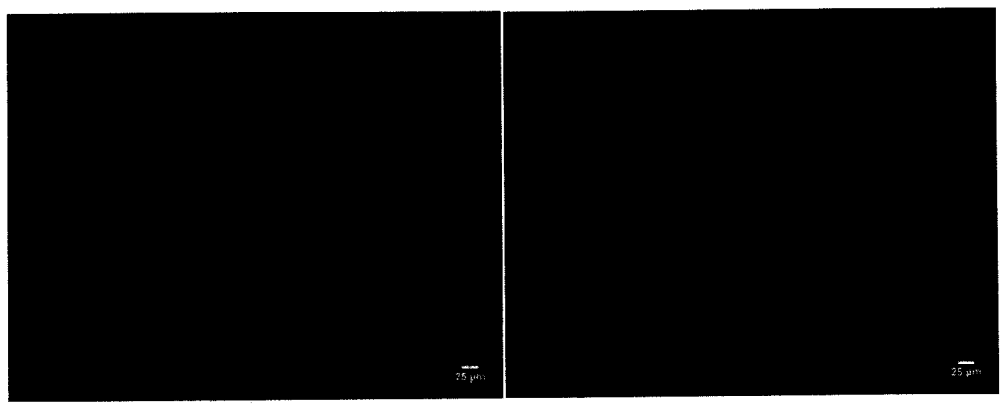
FIG. 17 is photographs of stained cells using the 0.4 μm insert of the wells prior to scraping (left) and post scraping (right)

After completing the staining, the 0.4 micron wells were analyzed with an inverted fluorescent microscope. When examining the wells prior to scraping them, it was apparent that there were still cells on the membrane, either on the upper or lower surface. After scraping the upper surface with a q-tip, the wells were re-examined, which showed evidence of no cell migration to the opposite side of the well. FIG. 17 contains representative images of the 0.4 micron wells, both before and after scraping.

Figure 18:
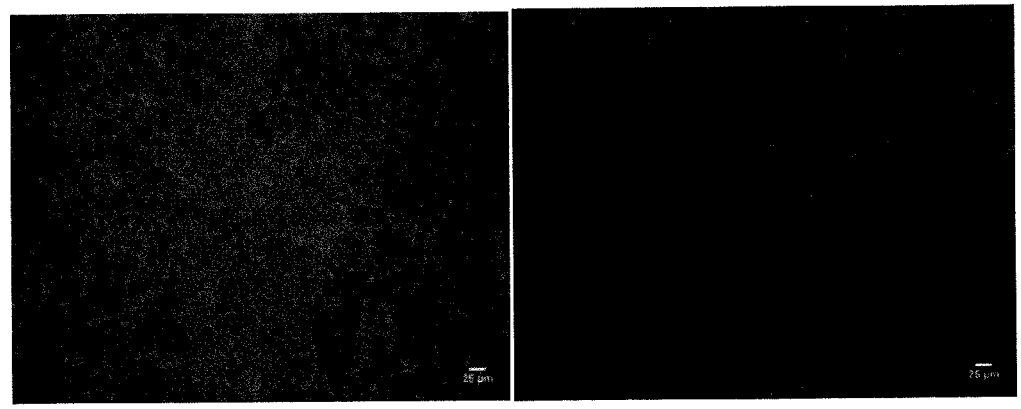
FIG. 18 is photographs of stained cells using the 3 μm insert of the wells prior to scraping (left) and post scraping (right)

Similar to the 0.4 micron wells, an initial look with the scope revealed amass of cells on the 3 micron wells. However, after scraping the wells with a q-tip, there was still a significant amount of cells. This confirms the belief that the 3 micron pores are too large, which allow for the cells to migrate through to the other side. FIG. 18 below shows the representative images.

Scaffold Gap Junction Formation Assay

Figure 19:
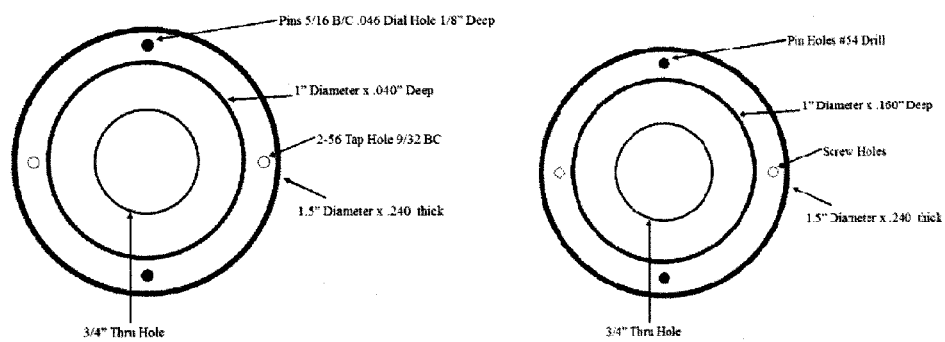
FIG. 19 is a diagrammatic representation of the Gaudette-Pins Dual Transwells.

A Transwell assay for gap junction formation across a polyurethane microporous membrane was performed. One layer of hMSC cells was seeded on each side of the microporous polyurethane membrane. See FIG. 19 for assay representation. Using connexin 43 staining and confocal microscopy it was possible to determine gap junction formation across the pores. After seeding and the appropriate tracking (quantum dot) the system was incubated for 48 hours and stained for connexin 43. See FIG. 19 for design specification of custom built dual well for gap junction assay.

Figure 20:
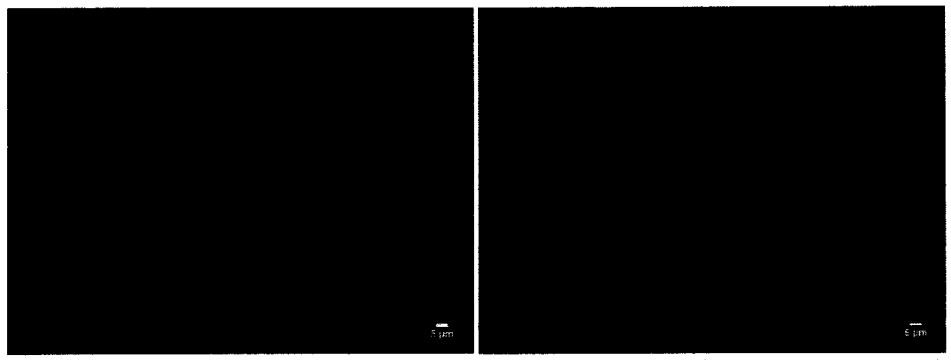
FIG. 20 is photographs of stained cells at 40× magnification, positive (left) and negative (right) tissue control slides.
Figure 21:
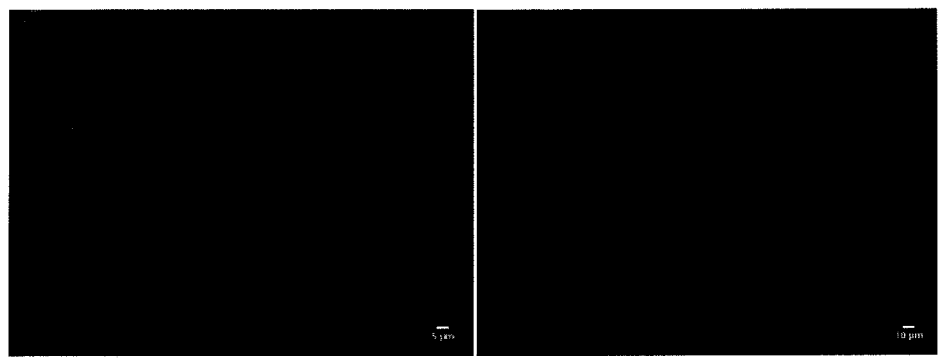
FIG. 21 is photographs of stained cells, positive cell samples at 40× (left) and 20× (right)

Connexin 43 (the primary protein in gap junctions) staining was conducted on fixed cells blocked with 1.5% Normal Rabbit Serum (NRS). The primary antibody was mouse anti-connexin at 1:250 concentration in 1.5% NRS and the secondary antibody was Alexa Flour 488 rabbit anti-mouse at 1:400 concentration in 1.5% NRS. The cells were DAPI counterstained. FIGS. 20 and 21 are representative images of tissue controls and cell samples.

Figure 22:
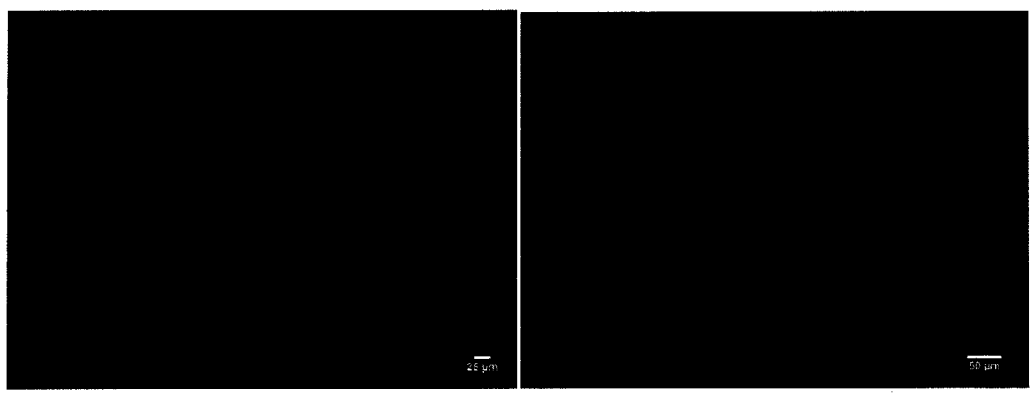
FIG. 22 is photographs of stained cells, dead (left) and live (right)

Cell viability on the polyurethane scaffold was determined via Live/Dead staining. For live hMSCs the fluorescent dye calcein was used at a concentration of 1 µMolar. For dead hMSCs, Ethidium Bromide was used at a concentration of 8 µMolar. FIG. 22 shows representative images of Live/Dead staining results.

Chronoflex® C polyurethane pellets were electrospun into thin microporous sheets. The distance from the needle to the collecting plate for spinning was 15 cm. If this distance is increased, the result is thinner fibers and thinner pores. While electrospinning the material, a 10% weight to volume ratio of polyurethane was used. A 20 kV voltage was applied to the polyurethane which was sprayed out at a rate of 3 mL/hr. Polyurethane membranes were electrospun at three different time intervals: 30 minutes, 60 minutes, and 90 minutes (n=1 for each time). The average sheet thickness for a 60 minute electrospun sample was approximately 50 µm.

Results: Cell Viability Assay

Figure 23:
FIG. 23 is a photograph of stained cells.

The results from the cell viability assay showed a mixed bag of live and dead fluorescent signal. For the most part there was live signal as shown in FIG. 23. The controls had a much brighter signal for both live and dead. Live signal is represented by green while dead cells show up as red. The polyurethane isn't completely transparent so it could have played a role in the reduced signal. In addition, the formation of gap junctions among the cells demonstrated cell viability on the polyurethane.

Results: Gap Junction Assay

Figure 24:
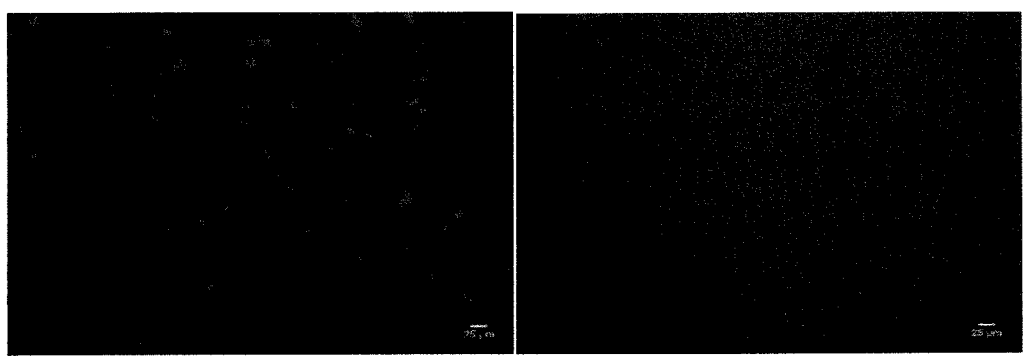
FIG. 24 is a photograph of human Mesenchymal Stem Cells on one side of the polyurethane sheet after 3 days incubation (left) and the reverse side of the same polyurethane sheet showing no cell migration (right)
Figure 25:
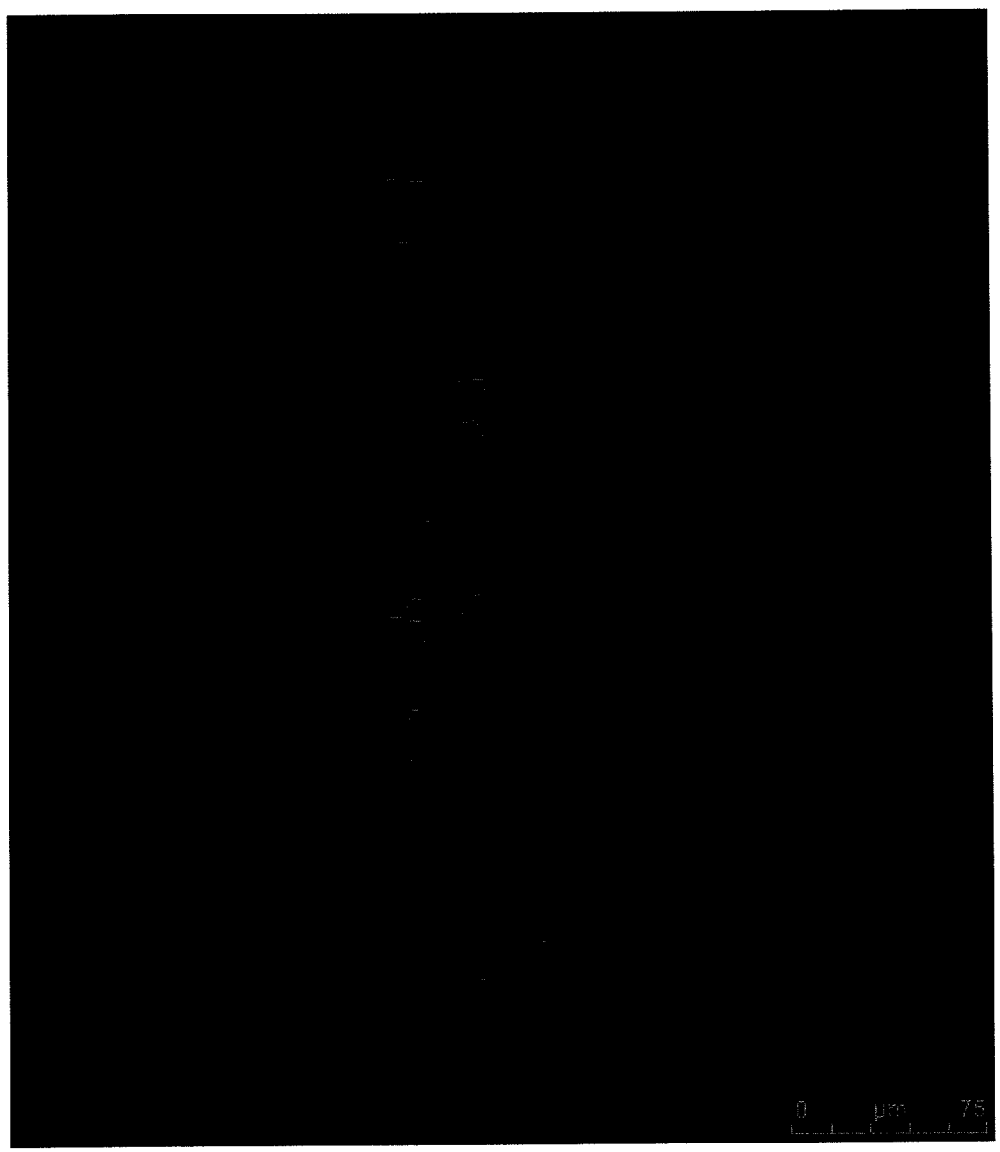
FIG. 25 is a photograph of cells labeled with connexin showing 3D gap junction formation through a polyurethane sheet.

Cells were seeded on both sides of the polyurethane scaffold suspended in the Gaudette¬ Pins dual well and allowed to incubate for 48 hours. Staining with controls was conducted as out lined in the methodology. Confocal microscopy was used to determine gap junction formation through the polyurethane. Confocal microscopes allowed for visualization in the x-, y-, and z¬ planes, FIG. 24 shows a 3-D projection of the cell seeded polyurethane. The nuclei (blue circles) on the far sides represent cells on opposite sides of the polyurethane. As seen in FIG. 25 there is nuclei signal and gap junction (green) signal between the polyurethane scaffolds. The results demonstrate that formation of gap junctions through the scaffold is possible.

Results: Migration through Polyurethane

One of the potential limitations with the electrospun polyurethane is the lack of a precisely controlled pore size. In order to ensure that the gap junctions seen in the previous assay were formed through a barrier that limited migration, another migration assay was conducted. All test parameters remained the same, except this time the specially manufactured wells were used. Quantifying migration for this round of experiments was less complicated because the polyurethane sheets were not transparent. Therefore, no scraping was necessary; when being examined with the fluorescent scope, the custom made well was flipped over to examine the other side.

Results showed that no cells were able to pass through the 30, 60, or 90 minute electrospun microporous sheets. FIG. 24 shows the difference between the side of 60 minute sheet on which cells were seeded, and the opposite side (where the hMSCs could not migrate to).

Electrospinning of Flat Polyurethane Sheets (nPU)

Methodology:

A polyurethane polymer solution was prepared in ice-cold 100% HFIP. This polymer solution was mixed on an inversion mixer for 48 hours in order to completely solubilize the polyurethane (PU) chips. A novel self-contained, computer automated electrospinning apparatus was developed. This system consists of a Glassman power supply, a Harvard Apparatus syringe pump, a custom-designed polyethylene chamber, a spray head with power attachment, a reciprocating system and a motor-controlled mandrel rotator. Utilization of this system permits coating of the polymer onto the Aluminum sheet flat panel. A stainless steel 18-gauge blunt spinneret (0.5 mm internal diameter) was cut in half, with the syringe fitting end connected to the polymer-filled syringe. Nalgene PVC tubing was then connected to the syringe filled with the polymer solution followed by connection to the other half of the blunt spinneret within the spray head. The high potential source was connected to the spray head tip. The panel was set at a jet gap distance of 15 cm from the tip of the needle. The mandrel was then grounded to the power source. The perfusion rate was set at 3 ml/hour at 25° C. Perfusion of the polymer was then started upon application of the current to the tip of the needle (+25 kV) with electrospinning (espin) proceeding for either 15, 30, 40 or 60 minutes. After electrospinning, the nanofibrous PU sheets (nPU) was sprayed with 70% ethanol, allowed to sit for 5 minutes, removed from the panel and immediately exposed to 100% ethanol for 30 minutes with sonication followed by a 2 minute sonication in distilled water in order to remove the residual HFIP solvent.

Figure 26:
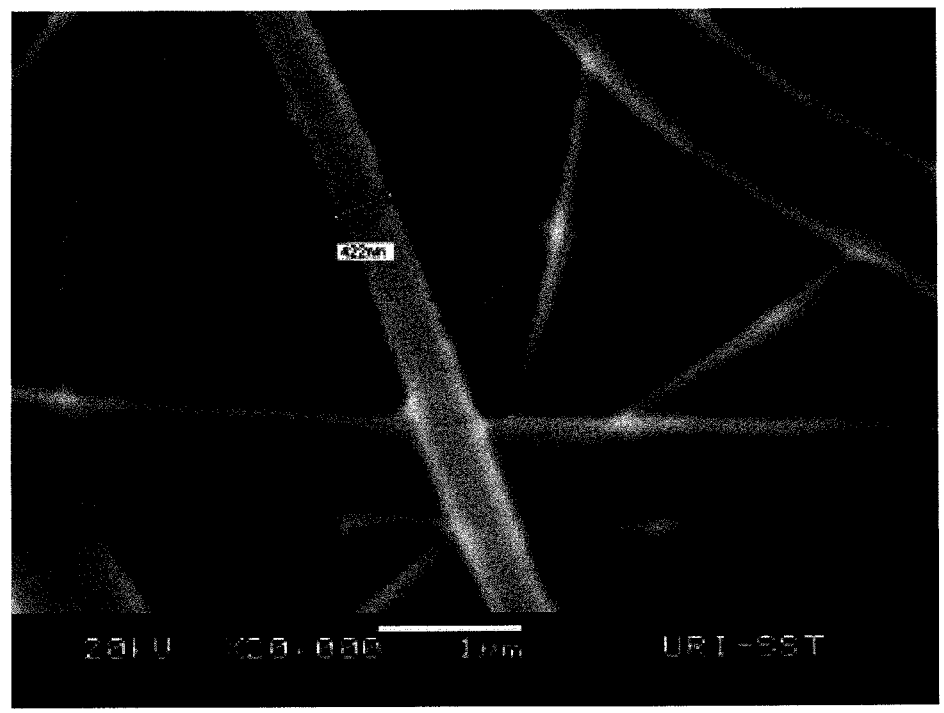
FIG. 26 is a scanning electron micrograph of espun polyurethane sheet.

Results:

Circular segments (16 mm diameter) were cut using a custom mallet die (Texas Dies). Segments were evaluated for thickness using an Ames digital micrometer and weighed. Average range of thickness and weight of segments were: 15 minute, 20-80 micrometers (µm), 2-6 milligrams (mg); 30 minute, 90-150 µm, 10-15 mg; 40 minute, 150-200 µm, 12-17 mg; 60 minute 200-250 µm, 13-20 mg. E-spun sheets had consistent white appearances with no bubbling or obvious irregularities. The major variable was surface area deposition. A small deposition area meant thicker, heavier samples for the same given spinning time. This was addressed by starting the collecting plate flat and limiting rotation to a couple degrees in either direction. Scanning electron microscopy was done on all spin times and average fiber diameters of 500 nm-3 µm (FIG. 26).

Nanofibrous polyurethane scaffolds (nPU) synthesized using the methods described herein can be modified to encapsulate various cell types. Parameters such as electrospinning time or gap distance can be increased in order to create a thicker membrane or fiber diameter, respectively in order to achieve the desired outcomes (no cell permeation, cell viability and specific protein permeation through the matrix). All such nanofibrous scaffolds can be ethylene oxide (EtO)-sterilized as described herein.

Cell Viability on nPU Sheets

Figure 27:
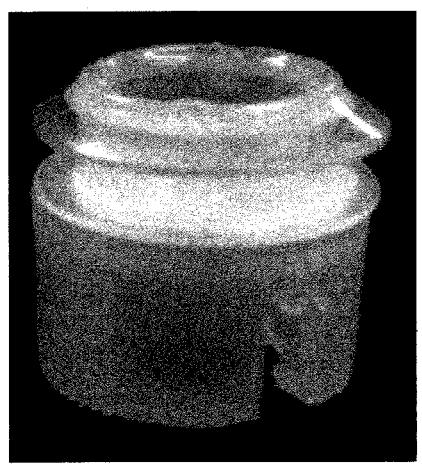
FIG. 27 is a photograph of a custom cell seeding chamber ("BioSeeder")

Methodology:

Cell viability and cellular migration were assessed using a custom seeding chamber (BioSeeder; FIG. 27) and nPU sheets electrospun for 15, 30, 40 and 60 minutes. nPU sheets were loaded into individual BioSeeders, placed into 12 well plates and ethylene oxide sterilized. Four time intervals (24, 48, 96, 192 hrs) were assessed for each nPU with varying espin times. Basic fibroblast growth factor[j] (bFGF (Peprotech))-loaded human mesenchymal stem cell (MSC) growth media (Lonza; 30 ng/ml) was placed into each well of the tissue culture plate in order to contact the bottom surface of each nPU material to promote MSC chemotaxis. Human MSCs (60,000 cells; P6; Lonza) were then seeded into upper chambers of the BioSeeder with non-FGF loaded growth medium. After the respective time interval, nPU samples were taken out of incubator and stained to determine hMSC viability using a LIVE/DEAD Viability/Cytotoxicity Kit for mammalian cells (Invitrogen). Samples were viewed with a Leica DMIL inverted fluorescent microscope. The nPU autofluoresced under the TX Red and while dead signal was distinguishable, all images were post processed with ImageJ software so both live and dead signal was clear.

Figure 28:
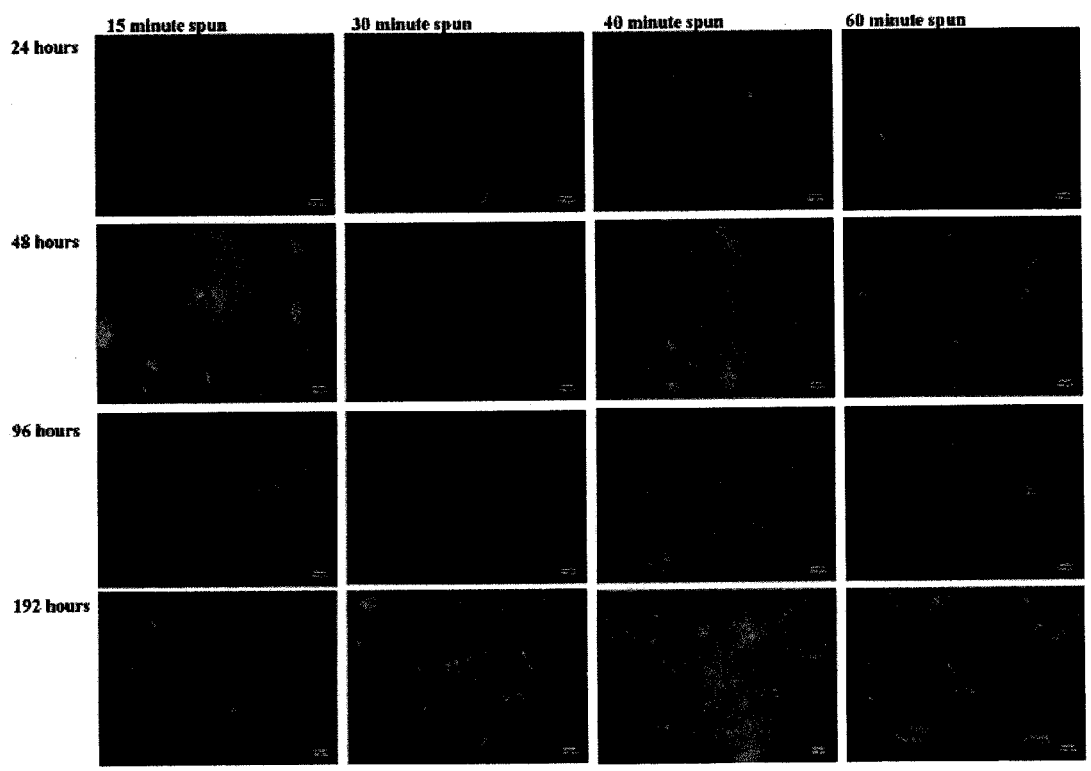
FIG. 28 is photographs of stained cells showing cell viability on nPU sheets.

Results:

Cell viability was evidenced by green signal greater than red signal on all segments (FIG. 28). These results indicate that hMSCs remain viable on nPU for at least 192 hours. In some of the earlier time intervals, cells would bunch and collect heavily on only one corner of the nPU. However, with the 192 hr samples, there was cell distribution over the entire surface for all samples suggesting hMSC growth on the nPU. With the samples looking more confluent at each time interval, the next logical step is to consider whether the cells are able to grow or migrate through the nPU material.

Cell Migration Through Polyurethane Sheets

Methodology:

The bottom side (side opposite of cell seeding) was imaged on all samples. The only change to the settings was the exposure time (631.8 milliseconds).

Figure 29:
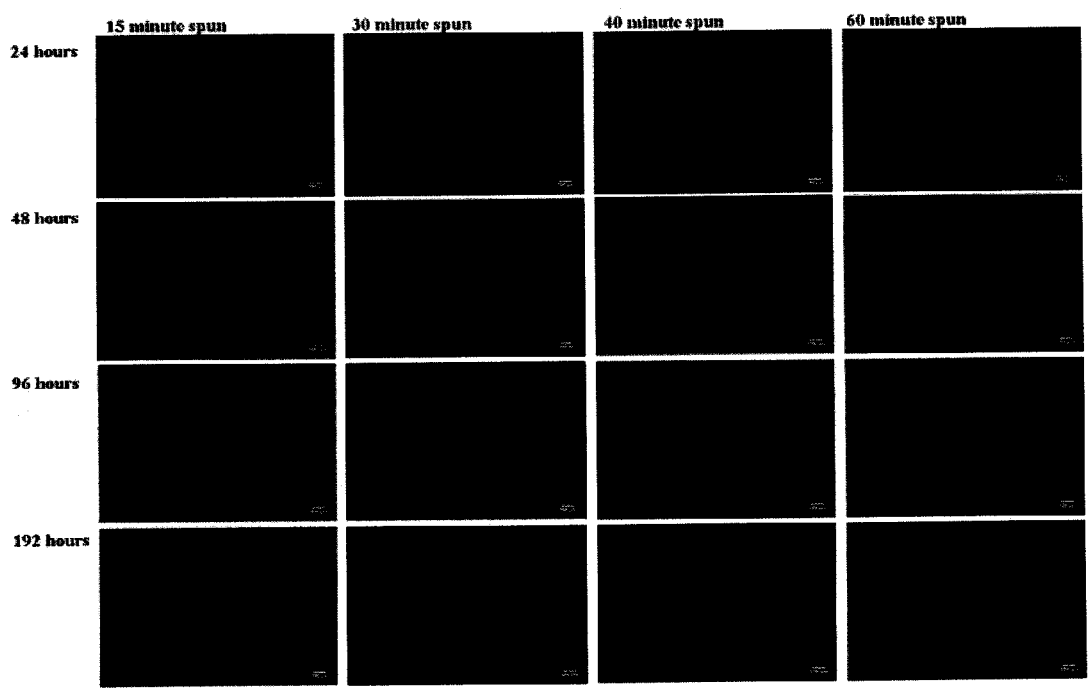
FIG. 29 is photographs of stained cells showing inhibition of cell migration through nPU sheets.

Results:

hMSCs migrated through the 15 minute espin time samples at all time points (FIG. 29). There was no evidence of migration on any of the 30, 40 or 60 minute espin time samples for all respective time intervals. The thickest 15 minute sample was 60 µm while the thinnest 30 minute sample was 90 µm. Therefore, samples over 90 µm thick may prohibit hMSC migration for at least 192 hours.

Dye Permeation through PU Sheets

Figure 30:
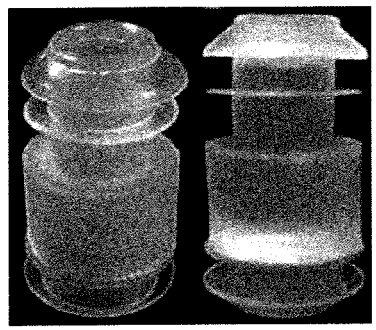
FIG. 30 is a photograph of a custom well for permeation studies ("BioPermeator")
Figure 31:
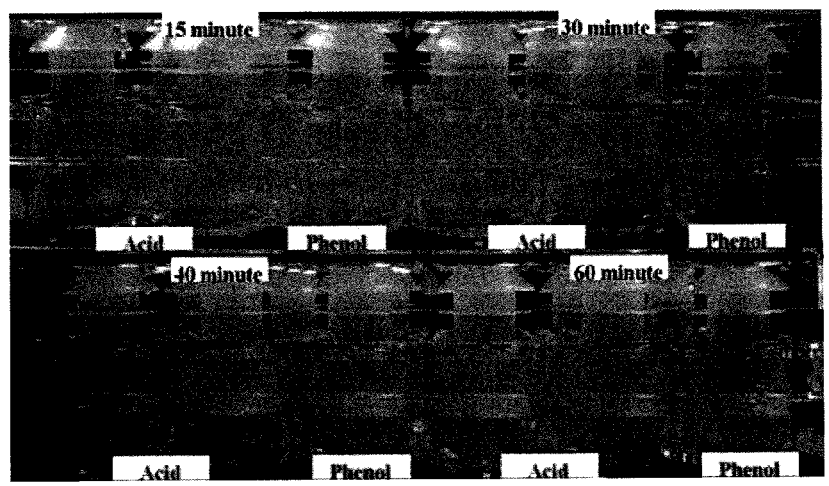
FIG. 31 is a photograph of the BioPermeators showing acid red and phenol red in top compartment at 0 hr incubation time.

Methodology:

Dyes Phenol Red and Acid Red 1 were used to determine if small molecular weight molecules were able to penetrate through nPU sheets of varying thickness over time. A modified BioSeeder (BioPermeator; FIG. 30) with a sealed bottom chamber was used. Sterile PBS (550 µL) was added to the bottom chamber. nPU circular samples (16 mm diameter), previously cut and measured for thickness, were sandwiched between the upper and lower halves of the BioPermeator. One milliliter of either Acid Red 1 dye or smooth muscle growth media (with Phenol Red indicator, Lonza) was added to the top chamber and then sealed with Parafilm. BioPermeators were created for each electrospin time of 15, 30, 40 and 60 minutes (n=3 segments/electro spin time). BioPermeators were placed into a 24 well tissue culture plate and incubated in a humidified 37° C. environment. At 0 (FIG. 31), 1, 2, 4, 6, 24 and 48 hours, the plate was removed and photographed.

Figure 32:
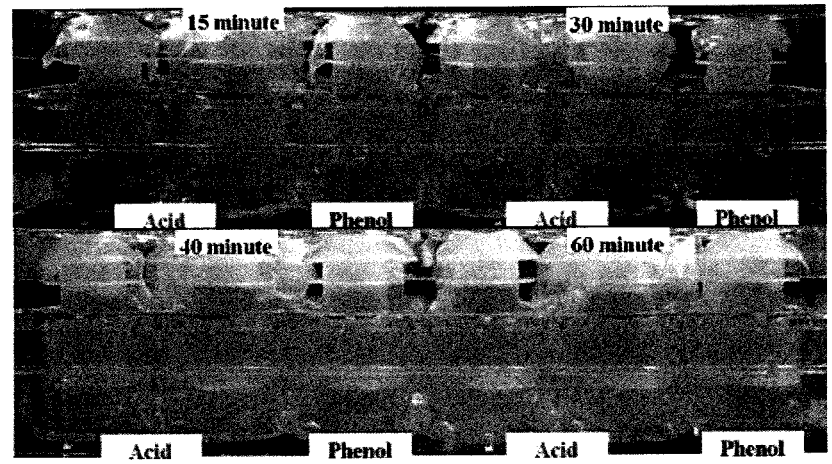
FIG. 32 is a photograph of the BioPermeators at 48 hr incubation time showing phenol red permeated nPU sheets for all espin times and acid red permeated nPU sheets for all espin times except 40 and 60 minutes.

Results:

By 48 hours (FIG. 32) there was clear indication of permeation of phenol red (376 g/mol) in all the samples and of acid red (509 g/mol) permeation in all samples except for the 40 and 60 minute espin times. The next step was to determine whether larger proteins can permeate through the nPU.

Protein Permeation through PU Sheets

Methodology:

Permeation of bovine serum albumin (BSA; 66 kDa) and thyroglobulin (660 kDa) through nPU sheets was evaluated using nPU segments electrospun for 15, 30, 40 and 60 minutes. Segments were measured for weight and thickness. Each protein (1 mg/ml) was prepared in sterile PBS. A total of 3 runs were performed for each spin time and protein. Sterile PBS (550 µL) was pipetted into the lower chamber of the BioPermeators. nPU segments were sandwiched between the lower and upper chambers. Each protein solution (900 µL) was then pipetted into the upper chamber of the BioPermeator, with the device sealed with Parafilm. BioPenneators were placed into a 24 well tissue culture plate and incubated in a humidified 37° C. environment. After 48 hours, solutions from all upper and lower chambers of BioPermeators were measured for volume and transferred into separate Eppendorf tubes. A Lowry protein assay was done on all solution samples in order to determine protein amounts in each chamber of the well.

Figure 33:
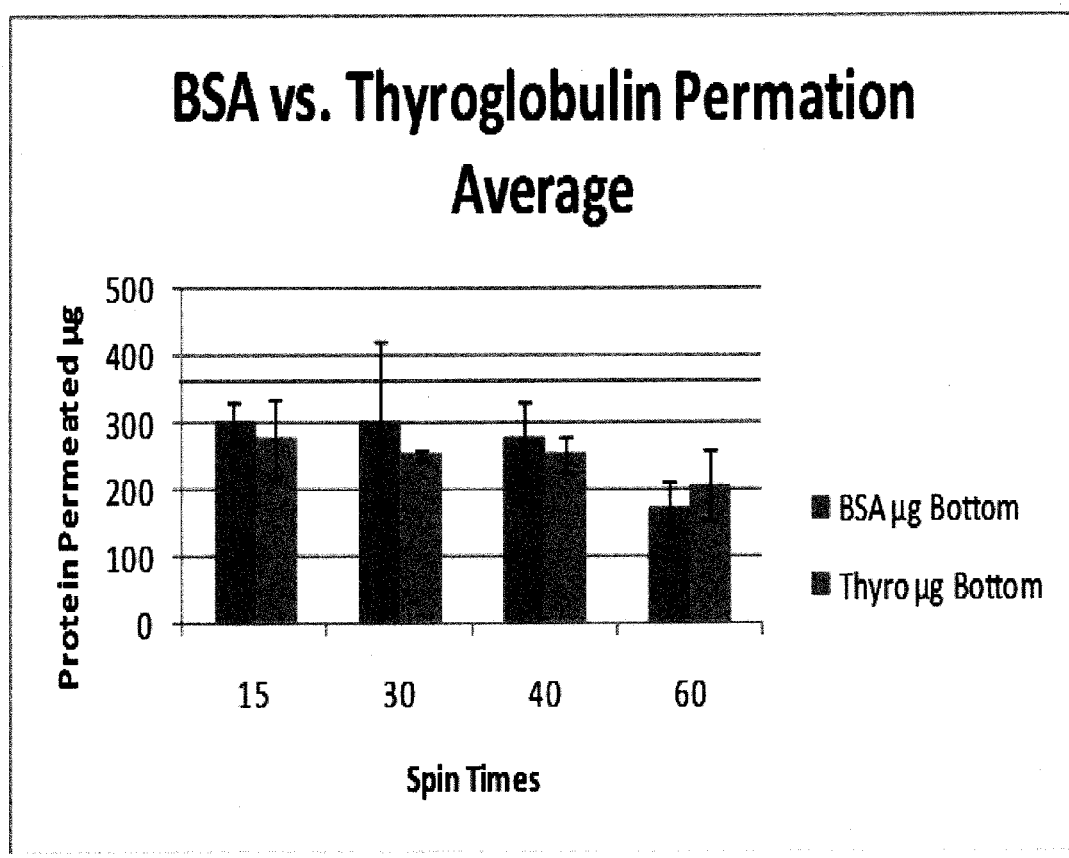
FIG. 33 is a bar graph showing BSA and thyroglobulin permeation through nPU sheets.

Results:

There were detectable amounts of both proteins in all lower chambers, indicating protein diffusion across the membrane. Despite being ten times larger, thyroglobulin was detected at similar concentrations as BSA. The mean protein value for each condition is graphed in FIG. 33. The theoretical equilibrium amount of protein in the bottom chamber taking into account complete diffusion would be 353 µg. The 15, 30 and 40 minute electrospun nPU samples were comparable to this projected level. Taking into account protein and solution absorbed by the nPU material, the data indicates that 15, 30 and 40 minute electrospun polyurethane parameters permits free diffusion of proteins after incubation for 48 hours.

Protein permeation through nPU sheets will be conducted for 48 hours using Vascular Endothelial Growth Factor (VEGF, 45 kDa) and Neuregulin 1 (44 kDa). VEGF has been characterized in several studies as promoting angiogenesis while Neuregulin 1 has been reported to cause proliferation of terminally-differentiated cardiomyocytes. If there is minimal protein permeation detected as determined by Lowry Protein Assay, several longer incubation periods would be examined. Shorter time periods could also be assessed to further characterize the rate of protein permeation. If longer periods do not yield protein permeation, thinner nPU segments will be tested or electrospinning parameters could be modified to create larger fiber diameter, which would increase the overall porosity of the material.

Implantation

Figure 34:
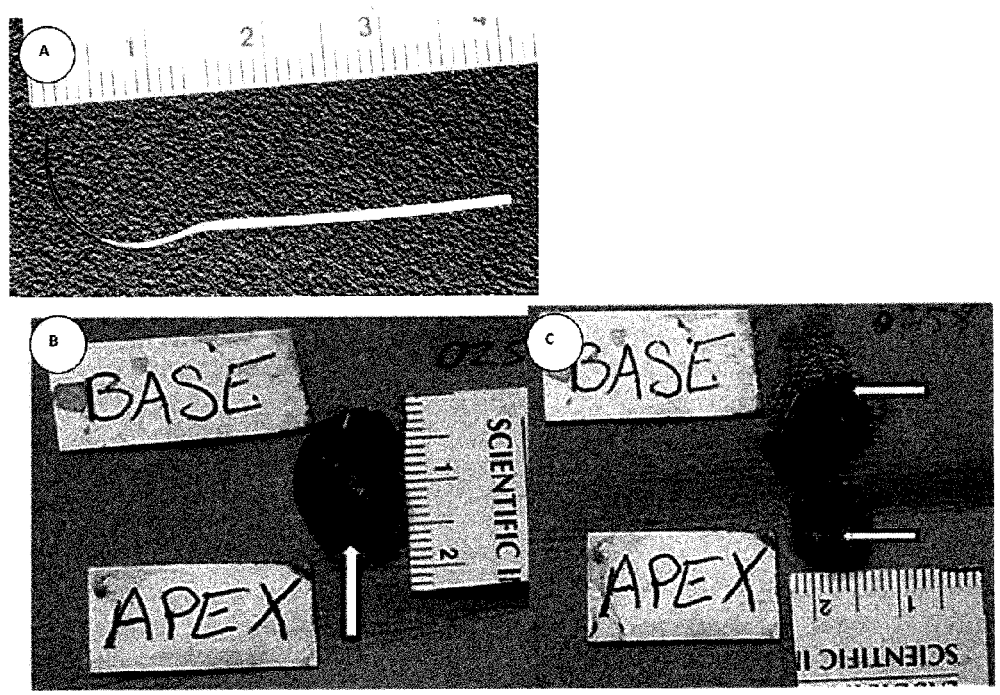
FIG. 34 is photographs of: A) the nano-fiber based scaffold formed in a cylinder and attached to a surgical needle; B) showing scaffold implanted in a rat heart from the base to the apex; and C) cross sectional view of nano-fiber scaffold implanted into heart (arrows document the location of the implanted scaffold)

To deliver the nano-fiber scaffold with hMSCs to the heart, a needle based delivery mechanism was developed. Polyurethane was electro-spun onto a cylindrical mandrel (O.D.=0.8 mm). This tube was threaded over a #20½ circle surgical needle (FIG. 34). The tube was then fixed to the needle by applying heat to the needle and allowing the tube to shrink onto the needle. The needle and tube was sterilized and delivered to the athymic rat heart (FIG. 34).

The scaffold could be pulled through the heart without any signs of mechanical failure. No signs of cardiac distress were noted. These data demonstrate a simple method for delivering nano-fiber scaffold that can be loaded with hMSCs.

Figure 35:
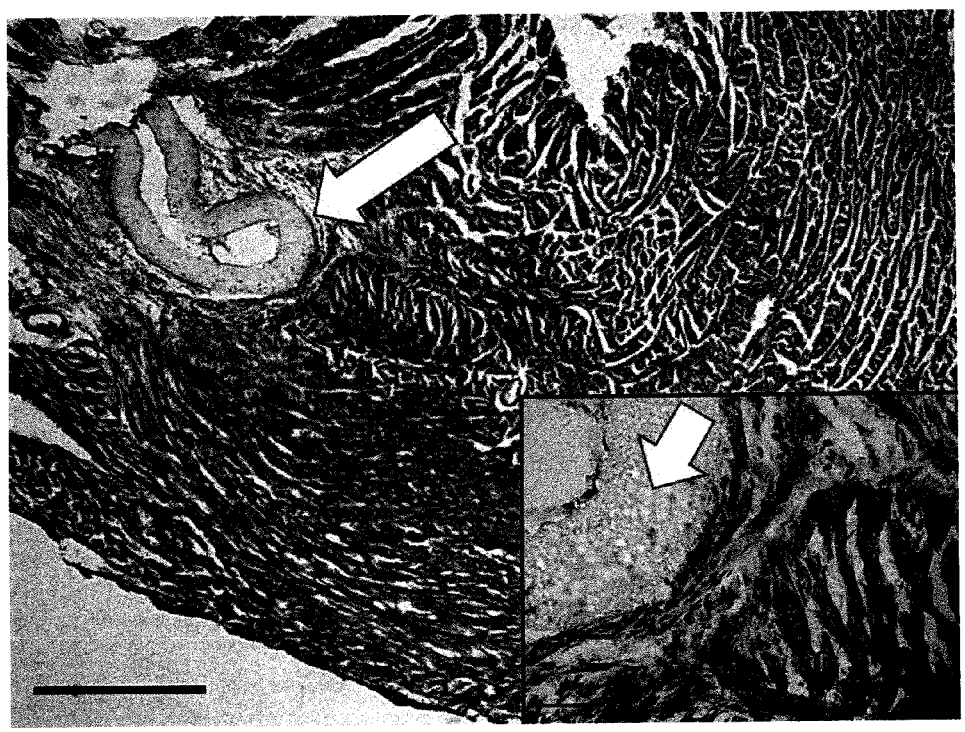
FIG. 35 is scanning electron micrographs of cross sections of a rat left ventricle showing the nano-fiber based scaffold after implantation in the rat heart for one week (arrow identifies the scaffold in the cross section; scale bar: 0.5 mm); the inset shows the proximity of the implanted scaffold to the native myocytes (scale bar 50 μm)

One week after implantation, the rat was euthanized and the heart removed. The scaffold could clearly be seen in the ventricular wall. The heart was then sectioned and stained with Masson's trichrome demonstrating minimal inflammation and fibrosis (FIG. 35). In this initial set of experiments the thickness of the delivered scaffold was much greater than that ultimately planned.

Characterizing Physical Properties of nPU Material

Tensile Testing:

nPU sheets (pre and post-EtO sterilization) will be cut into "dog-bone" shaped samples using a custom mallet die (Texas Custom Dies) for tensile testing. Segments (n=8 segments/ group) will be pulled at a strain rate of 50 mm/minute and force required to break the nPU materials determined. We anticipate, based on our previous data with nPU materials, that the force required to break these materials will range between 0.1 MPa and 1.9 MPa. These studies are also performed in order to determine if tensile properties are uniform across different lots of electrospun nPU sheets. If the tensile strength does not meet these specifications, synthesis parameters could be modified to alter the material composition (thicker/thinner wall).

Burst Strength:

A modified burst strength apparatus, developed for vascular graft constructs, will be employed in this study. For this apparatus, a stainless steel post containing a 7 mm (5/16 inch) ball bearing welded onto the end is mounted onto a 25 lb load cell. Using a rate of 30 mm/min, the compression force (kgf) required to puncture the material per thickness of the material will be determined. If compression force is not within specifications (4-5 kgf/mm), thicker samples will be synthesized.

Figure 36:
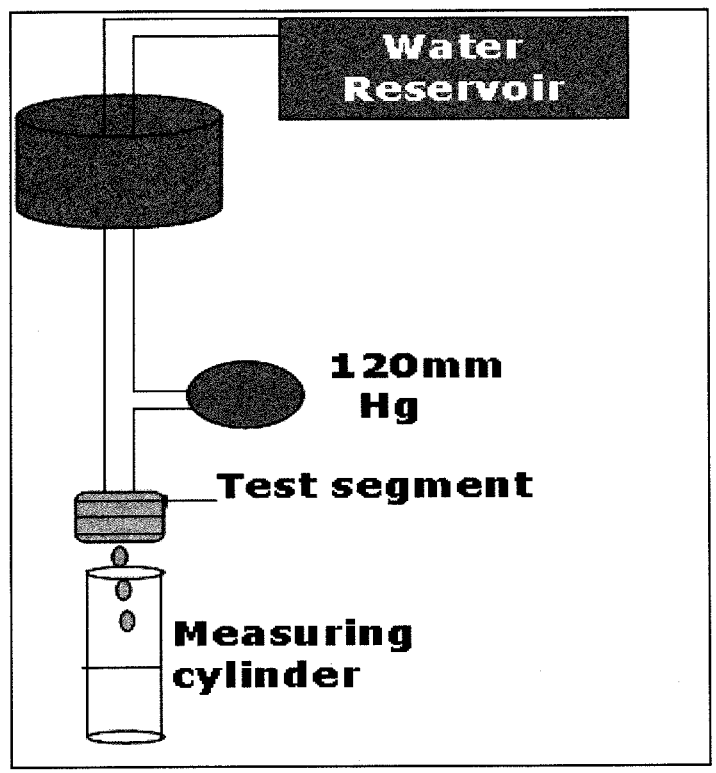
FIG. 36 is a diagrammatic representation of a water permeation apparatus.

Water Permeation:

nPU segments (n=8 segments) will be cut into 16 mm circular segments, weighed and measured for thickness. nPU segments will then be evaluated for water permeation using the apparatus shown in FIG. 36. The amount of water that passes through the sample in a minute is collected in a graduated cylinder. The flux is calculated in ml/min/cm$^2$. It is anticipated that, based on historic data for various nanofibrous materials evaluated by our group, the flux for the nPU material should be between 11-23 ml/min/cm$^2$. Again, espinning parameters could be adjusted to alter water permeation through the nPU material.

Prototype nPU Targeted Delivery Device (BioGenerator)

Figure 37:
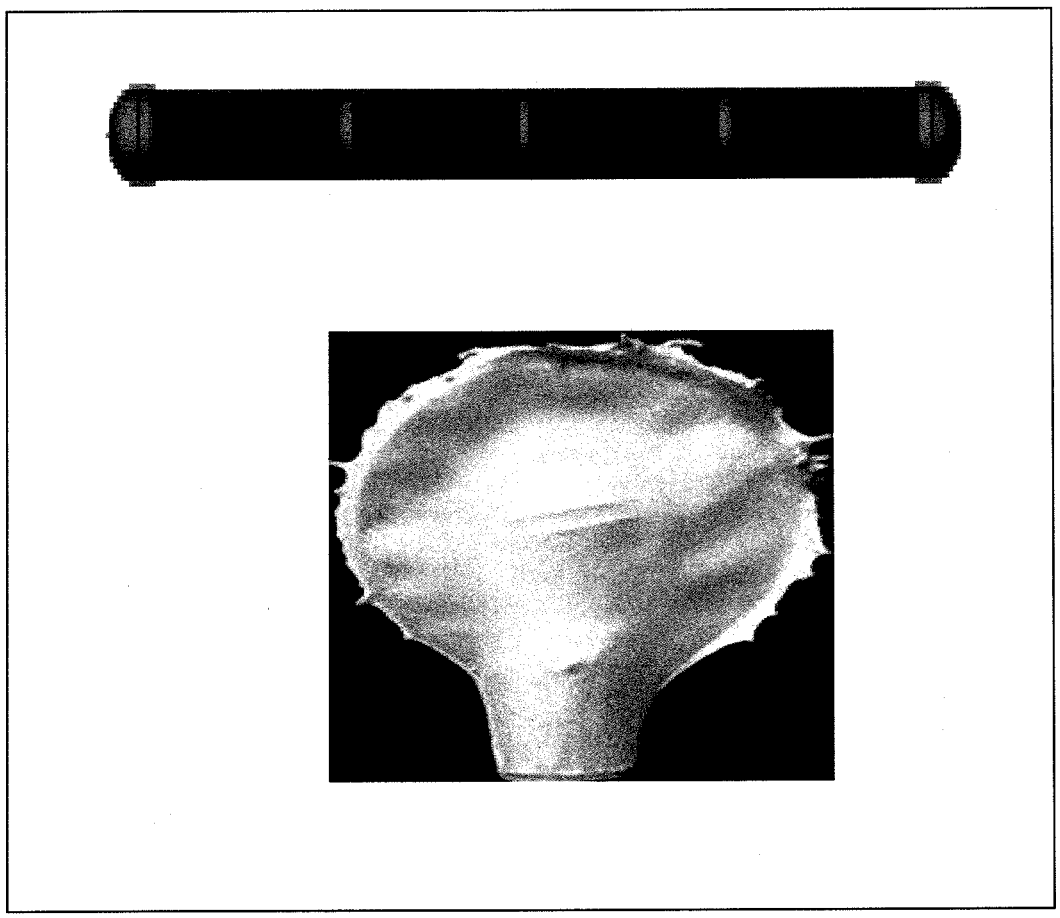
FIG. 37 is a diagrammatic representation of a cylindrical nano-fiber device of the invention and a disc shaped nano-fiber device of the invention.
Figure 38:
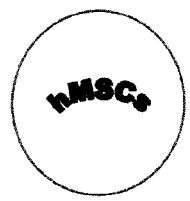
FIG. 38 is diagrammatic representations of designs of the nano-fiber device of the invention: A) represents a bag, i.e. nano-porous polymer material in the shape of a sphere; B) represents pancake-like discs, e.g. four layers of discs attached to the ventricular wall (anticoagulant coating facing ventricle, scaffold, cell layer, and nano-porous polymer mesh inhibiting cell migration); C) represents a three-layered mesh bag attached to the ventricular wall (blood compatible mesh encompasses both cells and attachment scaffold); D) represents a bi-layer pancake cap design; E) represents a flat mesh container design; and F) represents an open sided patch design where attachment dependent hMSCs stay on the scaffold with hMSC-free side available to interact with myocytes.
Figure 38:
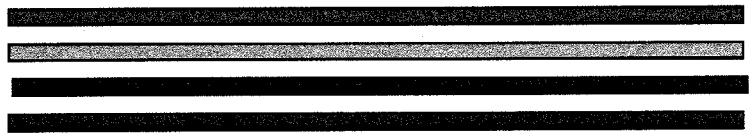
Figure 38:
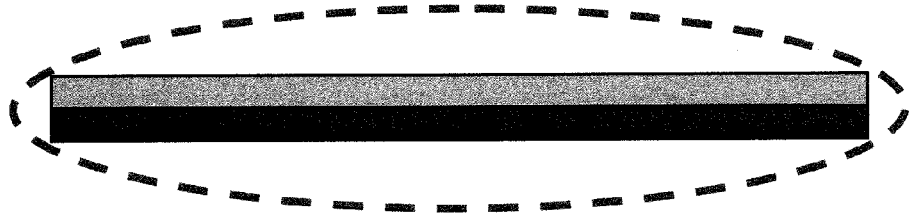
Figure 38:
Figure 38:
Figure 38:

A prototype (BioGenerator) will be developed using nPU and designed in terms of shape and production using the espinning technology and various possible mandrels acting as the collecting surface for the nPU material. Several overall design criteria will be utilized in developing the prototype. The first is simplicity of manufacture. The process needs to allow for simple spinning, post-treatment, EtO sterilization, cell seeding and in vivo delivery. The second design criteria involve size. Ideally, delivery of final device through endovascular means (e.g. catheter) because of the minimal invasiveness. However, the device could also be surgically implanted depending on the location within the patient's body in need of therapy or treatment. Potential designs include a disc shaped construct or a cylinder (FIG. 37). nPU will be espun over struts or applied to support members to create the device.

What is claimed is:

1. A device comprising a nanofibrous scaffold is 10-150 µm thick and contains pores that are 0.5-3 µm in diameter and immobilized cells.

2. The device of claim 1, wherein said nanofibrous scaffold is non-degradable.

3. The device of claim 1, wherein said scaffold comprises a synthetic material selected from the group consisting of nitinol, dacron, nylon, polytetrafluoroethyline, poly(glycolic acid), and polyurethane.

4. The device of claim 1, wherein said scaffold comprises electrospun polyurethane.

5. The device of claim 1, wherein said scaffold is in the form of a chamber or a layered sandwich.

6. The device of claim 5, wherein said chamber contains stem cells.

7. The device of claim 6, wherein said stem cells are human mesenchymal stem cells.

8. The device of claim 1, wherein said pores prohibit the migration of stem cells.

9. The device of claim 1, wherein said pores allow gap junction formation and protein diffusion.

10. The device of claim 1, wherein said pores are less than 3 µm in diameter.

11. The device of claim 1, wherein said pores are 2-2.5 µm in diameter.

12. The device of claim 1, wherein said nanofibrous scaffold is 10-20 µm thick.

13. The device of claim 1, wherein said nanofibrous scaffold is 30-60 µm thick.

14. The device of claim 1, wherein said nanofibrous scaffold is greater than 90 µm thick.

15. The device of claim 5, wherein said chamber shape is selected from the group comprising disc-shaped, cylindrical, oval, football-shaped and round.

* * * * *